US012172948B2

(12) United States Patent
Koley et al.

(10) Patent No.: US 12,172,948 B2
(45) Date of Patent: Dec. 24, 2024

(54) MOLECULAR PROBE FOR SELECTIVE DETECTION OF COPPER (II) IONS

(71) Applicant: Oregon State University, Corvallis, OR (US)

(72) Inventors: Dipankar Koley, Corvallis, OR (US); Partha Sarathi Sheet, Ann Arbor, MI (US)

(73) Assignee: Oregon State University, Corvallis, OR (US)

( * ) Notice: Subject to any disclaimer, the term of this patent is extended or adjusted under 35 U.S.C. 154(b) by 536 days.

(21) Appl. No.: 17/525,730

(22) Filed: Nov. 12, 2021

(65) Prior Publication Data

US 2022/0144758 A1 May 12, 2022

Related U.S. Application Data

(60) Provisional application No. 63/113,029, filed on Nov. 12, 2020.

(51) Int. Cl.
*C07C 251/80* (2006.01)
*G01N 21/25* (2006.01)
*G01N 21/64* (2006.01)
*G01N 27/333* (2006.01)

(52) U.S. Cl.
CPC ......... *C07C 251/80* (2013.01); *G01N 21/251* (2013.01); *G01N 21/643* (2013.01); *G01N 27/3335* (2013.01); *G01N 2021/6434* (2013.01)

(58) Field of Classification Search
CPC ............. G01N 21/643; G01N 27/3335; G01N 27/327–3272; G01N 27/40; G01N 2021/6434; C07C 251/80
See application file for complete search history.

(56) References Cited

U.S. PATENT DOCUMENTS

2010/0029773 A1* 2/2010 Bertsch .............. G01N 33/6896
435/7.1
2012/0316198 A1* 12/2012 Wiestner ................ A61P 31/00
546/284.7

FOREIGN PATENT DOCUMENTS

CN           105647512 A  *  6/2016  ............. C09K 11/06
WO   WO 2018017589 A1 *  1/2018  ........... A61K 31/343

OTHER PUBLICATIONS

EPO machine-generated English language translation of . CN 105647512 A, patent published Jun. 8, 2016 (Year: 2016).*
Gupta, Vinod K., Rajendra Prasad, and Azad Kumar. "Preparation of ethambutol-copper (II) complex and fabrication of PVC based membrane potentiometric sensor for copper." Talanta 60.1 (2003): 149-160.
Gupta, Vinod Kumar, et al. "A novel copper (II) selective sensor based on dimethyl 4, 4'(o-phenylene) bis (3-thioallophanate) in PVC matrix." Journal of Molecular Liquids 174 (2012): 11-16.
(Continued)

*Primary Examiner* — Alexander S Noguerola
(74) *Attorney, Agent, or Firm* — Christensen O'Connor Johnson Kindness PLLC

(57) ABSTRACT

Multifunctional dendritic molecular probes that selectively detect $Cu^{2+}$ ions via potentiometric and fluorometric techniques with low detection limits are disclosed. The selective and reversible binding of the molecules with the $Cu^{2+}$ ion was used to make solid-state microsensors by incorporating the molecular probes into the carbon-based membranes as an ionophore for Cu (II).

28 Claims, 21 Drawing Sheets

(56) References Cited

OTHER PUBLICATIONS

Que, Emily L., Dylan W. Domaille, and Christopher J. Chang. "Metals in neurobiology: probing their chemistry and biology with molecular imaging." Chemical reviews 108.5 (2008): 1517-1549.
Prohaska, Joseph R., and Anna A. Gybina. "Intracellular copper transport in mammals." The Journal of nutrition 134.5 (2004): 1003-1006.
Solomon, Edward I., et al. "Copper active sites in biology." Chemical reviews 114.7 (2014): 3659-3853.
Gaggelli, Elena, et al. "Copper homeostasis and neurodegenerative disorders (Alzheimer's, prion, and Parkinson's diseases and amyotrophic lateral sclerosis)." Chemical reviews 106.6 (2006): 1995-2044.
Bush, Ashley I. "Metals and neuroscience." Current opinion in chemical biology 4.2 (2000): 184-191.
Barnham, Kevin J., Colin L. Masters, and Ashley I. Bush. "Neurodegenerative diseases and oxidative stress." Nature reviews Drug discovery 3.3 (2004): 205-214.
Bull, Peter C., and Diane W. Cox. "Wilson disease and Menkes disease: new handles on heavy-metal transport." Trends in Genetics 10.7 (1994): 246-252.
Drinking Water Contaminants, U.S. EPA. (2009) 1-14.
Karadaş, Cennet, and Derya Kara. "Dispersive liquid—liquid microextraction based on solidification of floating organic drop for preconcentration and determination of trace amounts of copper by flame atomic absorption spectrometry." Food chemistry 220 (2017): 242-248.
Wei, Z., et al. "Determination of trace labile copper in environmental waters by magnetic nanoparticle solid phase extraction and high-performance chelation ion chromatography." Talanta 135 (2015): 155-162.
Wu, Jingfeng, and Edward A. Boyle. "Low blank preconcentration technique for the determination of lead, copper, and cadmium in small-volume seawater samples by isotope dilution ICPMS." Analytical chemistry 69.13 (1997): 2464-2470.
Galloway, N. McN. "Flame-photometric determination of iron, copper and cobalt in cobalt mattes and concentrates." Analyst 84.1001 (1959): 505-508.
Yu, Haitao, et al. "Porous-layered stack of functionalized AuNP-rGO (gold nanoparticles—reduced graphene oxide) nanosheets as a sensing material for the micro-gravimetric detection of chemical vapor." Journal of Materials Chemistry A 1.14 (2013): 4444-4450.
Ali, Akbar, Hong Shen, and Xuefeng Yin. "Simultaneous determination of trace amounts of nickel, copper and mercury by liquid chromatography coupled with flow-injection on-line derivatization and preconcentration." Analytica chimica acta 369.3 (1998): 215-223.
Coutinho, Cláudia FB, et al. "Direct determination of glyphosate using hydrophilic interaction chromatography with coulometric detection at copper microelectrode." Analytica chimica acta 592.1 (2007): 30-35.
Chen, Hong-Qi, et al. "Ultrasensitive determination of Cu 2+ by synchronous fluorescence spectroscopy with functional nanoparticles." Microchimica Acta 164.3-4 (2009): 453-458.
Zhao, Guangtao, et al. "An all-solid-state potentiometric microelectrode for detection of copper in coastal sediment pore water." Sensors and Actuators B: Chemical 279 (2019): 369-373.
Park, Suji, Claudia S. Maier, and Dipankar Koley. "Anodic stripping voltammetry on a carbon-based ion-selective electrode." Electrochimica Acta 390 (2021): 138855.
Singh, Ashok Kumar, Sameena Mehtab, and Ajay Kumar Jain. "Selective electrochemical sensor for copper (II) ion based on chelating ionophores." Analytica chimica acta 575.1 (2006): 25-31.
Huang, Shu-Wei, et al. "Synthesis of fluorescent carbon dots as selective and sensitive probes for cupric ions and cell imaging." Molecules 24.9 (2019): 1785.

Paul, Anirban, et al. "Fabrication of a Cu (II)-Selective Electrode in the Polyvinyl Chloride Matrix Utilizing Mechanochemically Synthesized Rhodamine 6g as an Ionophore." ACS omega 3.11 (2018): 16230-16237.
Bakker, Eric, Philippe Buhlmann, and Erno Pretsch. "Carrier-based ion-selective electrodes and bulk optodes. 1. General characteristics." Chemical Reviews 97.8 (1997): 3083-3132.
Bobacka, Johan, Ari Ivaska, and Andrzej Lewenstam. "Potentiometric ion sensors." Chemical reviews 108.2 (2008): 329-351.
Joshi, Vrushali S., et al. "Real-time metabolic interactions between two bacterial species using a carbon-based pH microsensor as a scanning electrochemical microscopy probe." Analytical chemistry 89.20 (2017): 11044-11052.
Johnson, R. Daniel, and Leonidas G. Bachas. "Ionophore-based ion-selective potentiometric and optical sensors." Analytical and bioanalytical chemistry 376.3 (2003): 328-341.
E. Bakker, "Electrochemical sensors," Anal. Chem., vol. 76, No. 12, Jun. 15, 2004, pp. 3285-3298.
Ummadi, Jyothir Ganesh, et al. "Carbon-based solid-state calcium ion-selective microelectrode and scanning electrochemical microscopy: a quantitative study of pH-dependent release of calcium ions from bioactive glass." Analytical chemistry 88.6 (2016): 3218-3226.
Chen, Hengwu, et al. "Flow injection on-line photochemical reaction coupled to spectrofluorimetry for the determination of thiamine in pharmaceuticals and serum." Analyst 123.5 (1998): 1017-1021.
Yadav, Neetu, and Ashok Kumar Singh. "Colorimetric and fluorometric detection of heavy metal ions in pure aqueous medium with logic gate application." Journal of The Electrochemical Society 166.8 (2019): B644.
Fu, Ying, et al. "A highly sensitive and selective fluorescent probe for determination of Cu (II) and application in live cell imaging." Spectrochimica Acta Part A: Molecular and Biomolecular Spectroscopy 208 (2019): 198-205.
Lan, Minhuan, et al. "Optically tunable fluorescent carbon nanoparticles and their application in fluorometric sensing of copper ions." Nano Research 12.10 (2019): 2576-2583.
Wang, Jiangru, et al. "Functional ZnS: Mn (II) quantum dot modified with L-cysteine and 6-mercaptonicotinic acid as a fluorometric probe for copper (II)." Microchimica Acta 185.9 (2018): 1-13.
Lu, Linlin, Guang Yang, and Yunsheng Xia. "From pair to single: sole fluorophore for ratiometric sensing by dual-emitting quantum dots." Analytical chemistry 86.13 (2014): 6188-6191.
Yu, Chunwei, et al. "Fluorescent probe for copper (II) ion based on a rhodamine spirolactame derivative, and its application to fluorescent imaging in living cells." Microchimica Acta 174.3 (2011): 247-255.
Park, Su Jeong, et al. "Calixazacrown ethers for copper (II) ion-selective electrode." Talanta 55.2 (2001): 297-304.
Su, Chia-Ching, Chuen-Her Ueng, and Lilian Kao Liu. "Characteristics of Lariat Crown Ether-Copper (II) Ion-Selective Electrodes." Journal of the Chinese Chemical Society 48.4 (2001): 733-738.
Sadeghi, S., et al. "Copper ion selective membrane electrodes based on some Schiff base derivatives." Electroanalysis: An International Journal Devoted to Fundamental and Practical Aspects of Electroanalysis 15.15-16 (2003): 1327-1333.
Szigeti, Zsófia, et al. "A novel polymeric membrane electrode for the potentiometric analysis of Cu2+ in drinking water." Analytica Chimica Acta 532.2 (2005): 129-136.
Kamata, Satsuo, et al. "Copper (II)-selective electrode using thiuram disulfide neutral carriers." Analytical Chemistry 60.22 (1988): 2464-2467.
Espada-Bellido, Estrella, et al. "Selective chemosensor for copper ions based on fluorescence quenching of a schiff-base fluorophore." Applied spectroscopy 64.7 (2010): 727-732.
Weng, Yan-Qin, et al. "A new selective fluorescent chemosensor for Cu (II) ion based on zinc porphyrin-dipyridylamino." Inorganic Chemistry Communications 10.4 (2007): 443-446.
Rahimi, Y., S. Shrestha, and S. K. Deo. "Metal affinity-based purification of a red fluorescent protein." Chromatographia 65.7 (2007): 429-433.

(56) References Cited

OTHER PUBLICATIONS

Kim, Hye-Seon, and Hee-Seon Choi. "Spectrofluorimetric determination of copper (II) by its static quenching effect on the fluorescence of 4, 5-dihydroxy-1, 3-benzenedisulfonic acid." Talanta 55.1 (2001): 163-169.
J. Coates, "Interpretation of Infrared Spectra, A Practical Approach," Encycl. Anal. Chem. (2000): 1-23.
Mohanan, K., M. Thankamony, and B. Sindhu Kumari. "Synthesis, spectroscopic characterization, and thermal decomposition kinetics of some lanthanide (III) nitrate complexes of 2-(No-hydroxyacetophenone) amino-3-carboxyethyl 4, 5, 6, 7-tetrahydrobenzo [b] thiophene." Journal of Rare Earths 26.4 (2008): 463-468.
Kamata, Satsuo, et al. "Copper (II)-selective membrane electrodes based on o-xylylene bis (dithiocarbamates) as neutral carriers." Analyst 114.9 (1989): 1029-1031.
Partha Sarathi Sheet, "Development of Dual Function Ionophore to Device a Cu (II) Micro-ISE," Sep. 10, 2020, Department of Chemistry, Oregon State University, 14 pages.
Partha Sarathi Sheet, "Development of Dual Function Ionophore to Device a Cu (II) Micro-ISE," Nov. 13, 2020, Department of Chemistry, Oregon State University, 14 pages.

\* cited by examiner

| Interfering ions | Selectivity coefficients (CMD) | Selectivity coefficients (Cu (II) ionophore I) |
|---|---|---|
| H⁺ | <-2.13 | - |
| Na⁺ | <-3.80 | -2.65 |
| K⁺ | <-3.15 | -2.35 |
| $Mg^{2+}$ | <-3.42 | -3.60 |
| $Ca^{2+}$ | <-3.09 | -3.60 |
| $Fe^{2+}$ | <-2.55 | - |
| $Co^{2+}$ | <-3.10 | -4.00 |
| $Zn^{2+}$ | <-3.00 | -2.25 |
| $Pb^{2+}$ | <-2.21 | -0.75 |

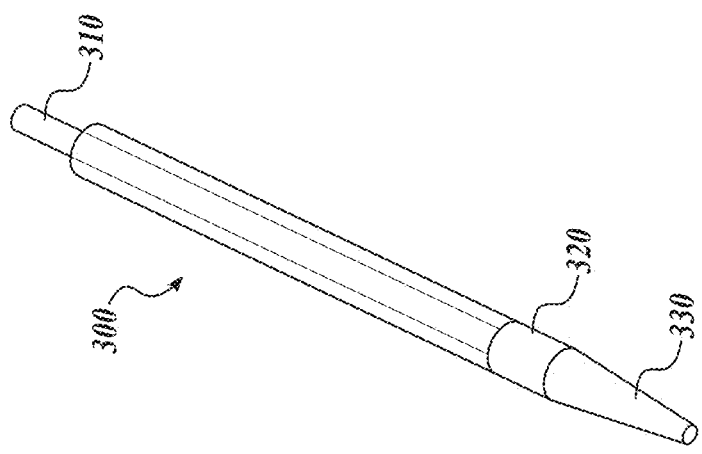
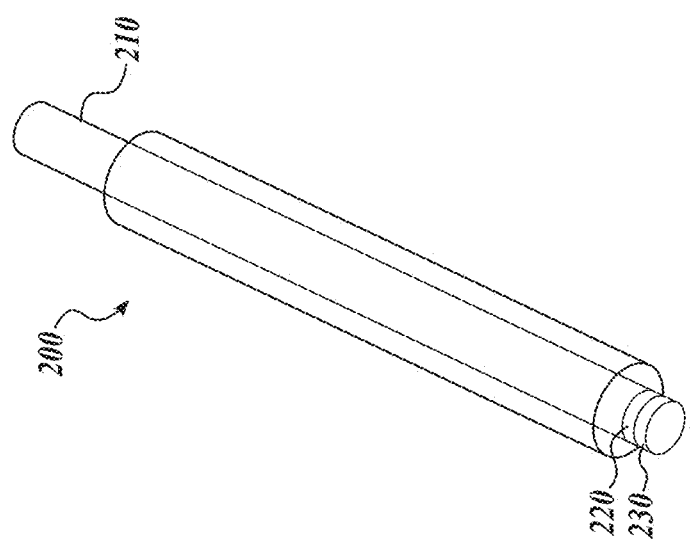
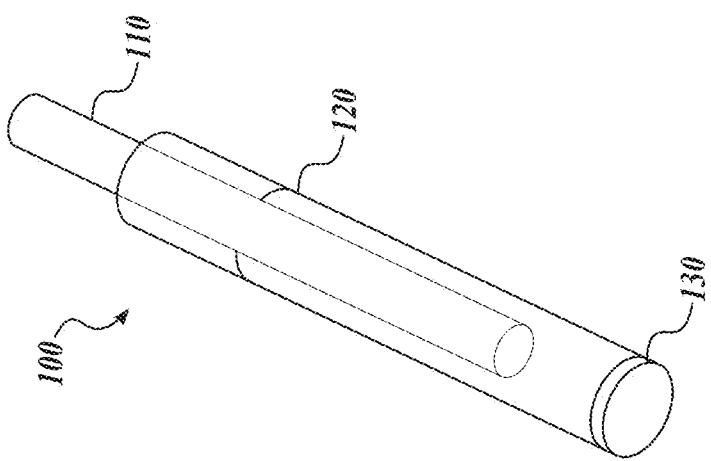

MOLECULAR PROBE FOR SELECTIVE DETECTION OF COPPER (II) IONS

CROSS-REFERENCE TO RELATED APPLICATION

This application claims the benefit of U.S. Application No. 63/113,029, filed Nov. 12, 2020, expressly incorporated herein by reference in its entirety.

STATEMENT OF GOVERNMENT LICENSE RIGHTS

This invention was made with government support under contract number R01DE027999 awarded by the National Institutes of Health. The government has certain rights in the invention.

BACKGROUND

Copper is a highly abundant element on Earth and has widespread use in various industries, such as electroplating, agriculture, wood preservation, and manufacturing, due to its corrosion resistance and good thermal and electrical conductivity. Copper plays an essential role in many biological processes, serving as a cofactor for many enzymes and being involved in metabolism regulation and protein activation. The total copper content in our body ranks third among the transition metal elements. The concentration of $Cu^{2+}$ in blood serum and the synaptic cleft is 10-25 μM and 30 μM, respectively. Nonetheless, excessive copper intake may cause Alzheimer's, Parkinson's, Wilson's, and Menkes disease. According to the US Environmental Protection Agency, the allowed concentration limit of $Cu^{2+}$ in drinking water is 1.3 mg/L (20 μM).

Numerous analytical techniques are available to detect trace quantities of $Cu^{2+}$, including atomic absorption spectrometry, inductively coupled plasma mass spectrometry, flame photometry, gravimetric detection, chromatography, fluorometry, and electrochemistry. Current limitations of these analytical techniques, however, are that they require sample pretreatment, involve complicated, bulky, expensive instruments and sophisticated procedures; are time-consuming for the routine analysis of multiple environmental samples, and necessitate highly trained personnel. Also, onsite monitoring of analytes is difficult with these techniques.

With a potentiometric ion-selective electrode (ISE), in contrast, analysis is simple, low cost, and portable due to its small size, which allows the ISE to be used onsite. The most crucial component of an ISE is the ionophore embedded in its polymeric membrane (usually made of polyvinyl chloride [PVC]). The ionophore has the unique capability of reversibly and selectively binding with the analyte ions. In addition to the potentiometric measurements made by using the ionophore in the ISE, fluorometric detection of Cu (II) by using a molecular fluorescence probe has been proven to be a versatile, selective, and sensitive method.

A 1,8-naphthalimide-based molecule has been designed having 320 nM of the detection limit for $Cu^{2+}$ detection (Y. Fu, X. X. Pang, Z. Q. Wang, Q. Chai, F. Ye, A highly sensitive and selective fluorescent probe for determination of Cu (II) and application in live-cell imaging, *Spectrochim. Acta—Part A Mol. Biomol. Spectrosc.* 208 (2019) 198-205). $Cu^{2+}$ sensing performance of carbon nanoparticles with 440 nM of detection limit has been introduced and optimized depending on the amounts of functional groups on the surface of the nanoparticles (M. Lan, S. Zhao, S. Wu, X. Wei, Y. Fu, J. Wu, P. Wang, W. Zhang, Optically tunable fluorescent carbon nanoparticles and their application in fluorometric sensing of copper ions, *Nano Res.* 12 (2019) 2576-2583). Other investigators have developed fluorescence probes by synthesizing or modifying the sensing molecules. However, the molecular capability of the fluorophores in the detection of single analytes using different methods often remains unexplored.

Existing Cu (II) ionophores have not been used as dual probes for potentiometry and fluorimetry. Moreover, problems have been described associated with selectivity against different metal ions, limiting their application in different areas. For example, a calixazacrown ether-based Cu (II) ionophore does not work below pH 7.0, and selectivity against common interfering ions such as alkali, alkaline earth, and most of the transition metal ions was not demonstrated; hence, it cannot be used in a situation where the pH value varies during detection. A lariat crown ether-based Cu (II) ionophore showed a super Nernstian slope of 42 mV/decade with a slow response time of 50 s, and no selectivity values were reported for alkali and alkaline earth metal ions (L. K. L. Su, Chia-ching, Chuen-Her Ueng, Characteristics of Lariat Crown Ether-Copper (II) Ion-Selective Electrodes, *J. Chinese Chem. Soc.* 48 (2001) 733-738). A Schiff base-based Cu (II) ionophore had poor selectivity against alkali metal (−3 or higher), alkaline earth metal (−2 or higher), transition metal ions (−1 or higher), that limits the use of this ionophore when it contains a high concentration of transition metal ions (S. Sadeghi, M. Eslahi, M. A. Naseri, H. Naeimi, H. Sharghi, A. Shameli, Copper Ion Selective Membrane Electrodes Based on Some Schiff Base Derivatives, *Electroanalysis.* 15 (2003) 1327-1333). A thiaglutaric diamide-based Cu (II) ionophore had very poor selectivity toward H+, and selectivity for most common interfering ions, such as $Fe^{2+}$, $Co^{2+}$ was not shown; these ions are known to bind to a sulfur center of an organic molecule, which will limit the use of this ionophore in water samples containing iron (Z. Szigeti, I. Bitter, K. Tóth, C. Latkoczy, D. J. Fliegel, D. Gunther, E. Pretsch, A novel polymeric membrane electrode for the potentiometric analysis of $Cu^{2+}$ in drinking water, *Anal. Chim. Acta.* 532 (2005) 129-136). A tetrabutyl thiuram disulfide-based Cu (II) ISE has been described as having an excellent detection limit (10 nM) but is not suitable for more than a day because of decomposition of the ionophore and low selectivity against $Zn^{2+}$ (−1.8), thus limiting the use of this ionophore in a solution containing a variable concentration of $Zn^{2+}$ (S. Kamata, A. Bhale, Y. Fukunaga, H. Murata, Copper (II)-Selective Electrode Using Thiuram Disulfide Neutral Carriers, *Anal. Chem.* 60 (1988) 2464-2467).

Despite the advances in the detection of copper ions, a need exists for improved compositions, devices, and methods for the detection of copper ions. The present invention seeks to fulfill this need and provides further related advantages.

SUMMARY

This summary is provided to introduce a selection of concepts in a simplified form that is further described below in the Detailed Description. This summary is not intended to identify key features of the claimed subject matter, nor is it intended to be used as an aid in determining the scope of the claimed subject matter.

In one aspect, the disclosure provides a compound of formula (I):

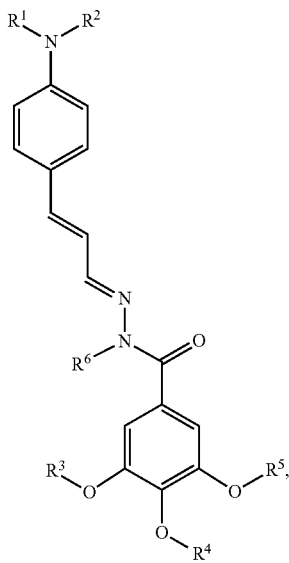

or a salt, an isomer, or tautomer thereof, wherein:

$R^1$, $R^2$, and $R^6$ are independently H, optionally substituted C1-C18 alkyl, optionally substituted C3-C18 alkenyl, optionally substituted C3-C18 alkynyl, optionally substituted C6-C18 aryl, or optionally substituted C5-C18 heteroaryl, and $R^3$, $R^4$, and $R^5$ are C1-C18 alkyl, C2-C18 alkenyl, or C2-C18 alkynyl, each of which is optionally substituted with a C6-C18 aryl or a C5-C18 heteroaryl.

In another aspect, the disclosure provides a membrane comprising a compound of formula (I).

In a further aspect, the disclosure provides a sensor comprising a compound of formula (I). The sensors of the disclosure include potentiometric, fluorometric, and colorimetric sensors and are selective for $Cu^{2+}$ ions.

DESCRIPTION OF THE DRAWINGS

The foregoing aspects and many of the attendant advantages of this invention will become more readily appreciated as the same becomes better understood by reference to the following detailed description when taken in conjunction with the accompanying drawings.

FIGS. 17A-17C are schematic diagrams of representative ion-selective electrodes (ISEs) of the disclosure: FIG. 17A illustrates a liquid contact ISE, and FIGS. 17B and 17C illustrate solid contact ISEs with the insulating membrane (17B) and conductive membrane (17C).

DETAILED DESCRIPTION

Figure 1:
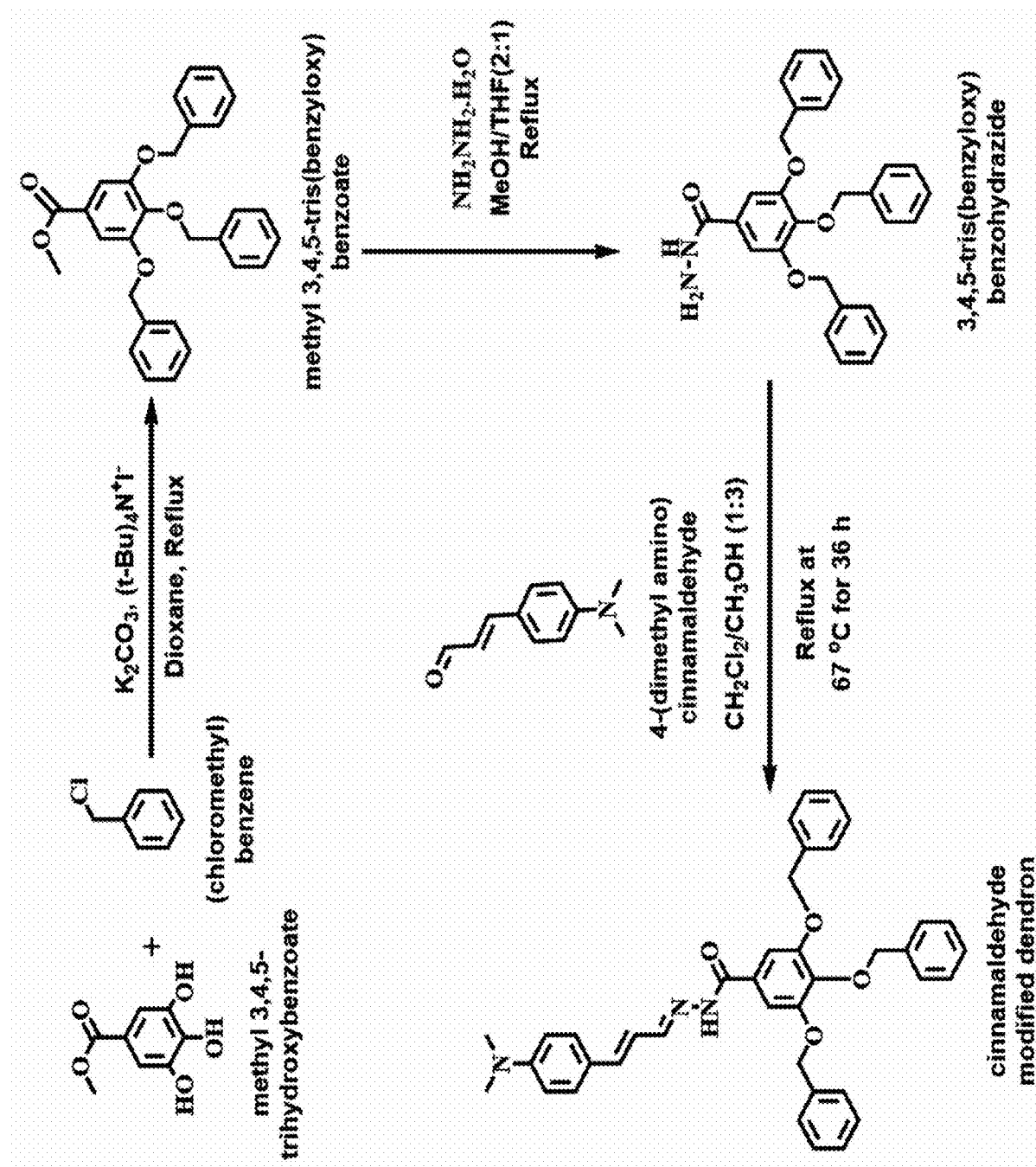
FIG. 1 shows synthetic route for preparation of an exemplary compound of formula (II) (also referred to as cinnamaldehyde modified dendron or CMD).

In one aspect, the disclosure provides a Cu (II) ionophore useful as a dual probe for potentiometry and fluorimetry.

With this ionophore, Cu (II) ion concentration is quantitated using a single multifunctional molecule for both potentiometry and fluorometry, instead of two separate molecules for each method. Furthermore, by incorporating a strong hydrophobic fluorophore, such as a cinnamaldehyde derivative, into the dendron molecule, the Cu (II) ionophore is also useful as a fluoroionophore for Cu (II).

The disclosure provides a Cu (II) ionophore molecule that is selective against major transitional metal ions in addition to alkali and alkaline earth metal ions. The dendritic ionophore provides reversible binding with Cu (II) by using a dendritic moiety along with an attached cinnamaldehyde component resulting in a multifunctional dendritic molecular probe for the selective and sensitive detection of Cu (II). The dendritic molecular probe can act as an ionophore for potentiometric methods, and incorporation of a cinnamaldehyde moiety in the ionophore allows it to become a fluorescent molecular probe to detect $Cu^{2+}$ ions. The selective and reversible binding of the molecule to $Cu^{2+}$ was used to make a solid-state micro-ion selective electrode (ISE) by incorporating the multifunctional ionophore into the carbon-based membrane to detect Cu (II) with high selectivity and fast response time.

The inventors of the present disclosure recognized the need for improved compositions and methods for detecting Cu (II) ions. In embodiments, the present disclosure describes compounds and compositions useful as a molecular probe capable of selectively detecting $Cu^{2+}$ ions via potentiometric, colorimetric, and fluorometric techniques with low detection limits.

In one aspect, the disclosure provides a compound of formula (I):

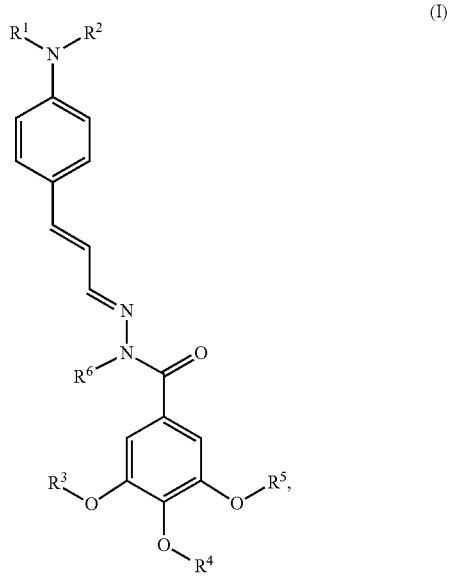

(I)

or a salt, an isomer, or tautomer thereof, wherein:
$R^1$, $R^2$, and $R^6$ are independently H, optionally substituted C1-C18 alkyl, optionally substituted C3-C18 alkenyl, optionally substituted C3-C18 alkynyl, optionally substituted C6-C18 aryl, or optionally substituted C5-C18 heteroaryl, and
$R^3$, $R^4$, and $R^5$ are C1-C18 alkyl, C2-C18 alkenyl, or C2-C18 alkynyl, each of which is optionally substituted with a C6-C18 aryl or a C5-C18 heteroaryl.

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms, it can be represented as 1-10C, as C1-C10, $C_1$-$C_{10}$, $C_{1-10}$, C-C10, or C1-10.

The terms "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as, for example, C3-C10, represents the sum of the number of carbon atoms in the cycle or chain and the number of such heteroatoms that are included as replacements for carbon atoms in the cycle or chain being described.

A single group can include more than one type of multiple bond, or more than one multiple bonds; such groups are included within the definition of the term "alkenyl" when they contain at least one carbon-carbon double bond, and are included within the term "alkynyl" when they contain at least one carbon-carbon triple bond.

"Aromatic" or "aryl" substituent or moiety refers to a monocyclic or fused bicyclic moiety having the well-known characteristics of aromaticity; examples include phenyl and naphthyl. Similarly, the terms "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. When heteroatoms are allowed to replace carbon atoms, the numbers describing the group, though still written as, for example, C5-C10, represent the sum of the number of carbon atoms in the cycle or chain and the number of such heteroatoms that are included as replacements for carbon atoms in the cycle or chain being described. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably, the monocyclic heteroaryls contain 5-6 ring members, and the bicyclic heteroaryls contain 8-10 ring members.

The moieties described above can be optionally substituted with a variety of substituents. "Optionally substituted," as used herein, indicates that the particular group being described may have one or more hydrogen substituents replaced by a non-hydrogen substituent, such as C1-C8 alkyl, C2-C8 alkenyl, C2-C8 alkynyl, C5-C12 aryl, C1-C8 acyl, and heteroforms of these, each of which can itself be further substituted; other substituents include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups.

In some embodiments of formula (I), the aryl and heteroaryl substituents are optionally substituted with one or more halogens.

In some embodiments, $R^3$, $R^4$, and $R^5$ are independently optionally substituted benzyl. In some embodiments, $R^3$, $R^4$, and $R^5$ are independently benzyl.

In some embodiments, $R^1$ and $R^2$ are independently H, methyl, or ethyl. In some embodiments, $R^6$ is H, methyl, or ethyl. In some embodiments, $R^6$ is H. In some embodiments, $R^1$ and $R^2$ are methyl.

In certain embodiments, the compound is:

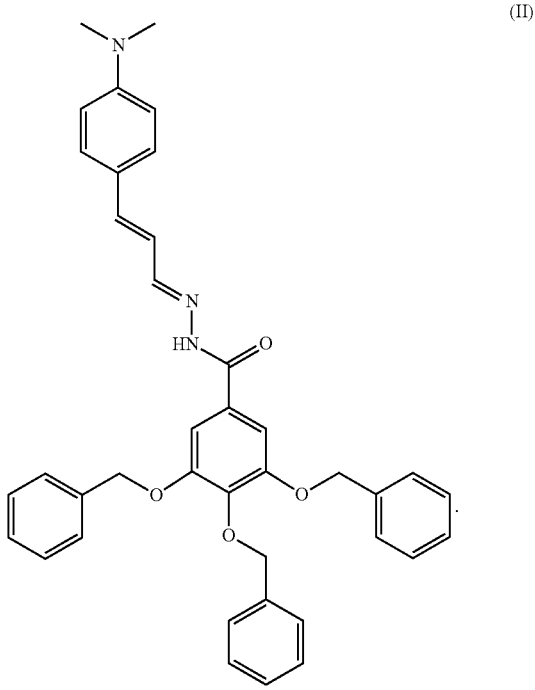 [SMILES: CN(C)c1ccc(/C=C/C=N/NC(=O)c2cc(OCc3ccccc3)c(OCc3ccccc3)c(OCc3ccccc3)c2)cc1]

(II)

The compounds of the disclosure selectively form a complex with a $Cu^{2+}$ ion in the presence of other cations. Thus, the compounds of the disclosure can act as Cu (II) ionophore molecules that are selective against major transitional metal ions in addition to alkali and alkaline earth metal ions. In some embodiments, the compound and/or the sensor are selective over $H^+$, $Na^+$, $K^+$, $Mg^{2+}$, $Ca^{2+}$, $Fe^{2+}$, $Co^{2+}$, $Zn^{2+}$, and $Pb^{2+}$ ions. Without being bound by theory, the compounds reversibly bind with Cu (II), thus acting as multifunctional dendritic molecular probes for the selective and sensitive detection of Cu (II). In some embodiments, the compound's fluorescence is quenched upon complexing with a $Cu^{2+}$ ion. In some embodiments, the compounds can act as an ionophore for potentiometric methods, as well as a fluorescent molecular probe to detect $Cu^{2+}$ ions.

In another aspect, provided herein is a carbon-based membrane comprising a compound of formula (I) or formula (II). The compound can be incorporated into the membrane by any suitable means, for example, the compound can be bound covalently or non-covalently (e.g., by hydrophobic interactions).

In a further aspect, the disclosure provides a sensor comprising a membrane and/or a compound of the disclosure. The sensors of the disclosure can be used as potentiometric, fluorometric, or colorimetric sensors. In some embodiments, the sensor is a potentiometric sensor with a $Cu^{2+}$ ion detection limit of about 3.5 μM or lower and/or a fluorometric sensor with a $Cu^{2+}$ ion detection limit of about 15 nM or lower.

In certain embodiments, the disclosure provides a Cu (II) selective electrode, comprising a solid electron conductor in electrical contact with an ion-selective polymeric composition comprising a compound of formula (I) or formula (II) (e.g., a carbon-based membrane of the disclosure). Any suitable electron conductor can be used in the electrodes of the disclosure, for example, a copper or other electroconductive wire.

In some embodiments, the Cu (II) selective electrode is a solid-state microsensor (e.g., a sensor having a diameter of about 25 μm) prepared by incorporating a compound of the disclosure into a carbon-based membrane as an ionophore for Cu (II). In some embodiments, the Cu (II) selective electrode of the disclosure has a high selectivity and fast response time.

In some embodiments, the Cu (II) selective electrode has a broad linear range, e.g., about 10 μM to about 1 mM, and/or a Nernstian slope or a near Nernstian slope (e.g., of 30 mV/log $[a_{Cu^{2+}}]$). In some embodiments, the Cu (II) selective electrode has a detection limit of about 0.1 μM, about 0.5 μM, about 1 μM, about 2 μM, about 3 μM, or about 4 μM. In some embodiments, the Cu (II) selective electrode has a fast response time (e.g., about 0.1 s to about 1.5 s). In some embodiments, the Cu (II) selective electrode has a broad working pH range (e.g., from about 3.5 to about 6.0).

In certain embodiments, the ion-selective composition or membrane of the sensors of the disclosure is prepared from a mixture that comprises: (a) tetraphenyl borate, tetrakis(4-chlorophenyl) borate, tetrakis[3,4-bis(trifluoromethyl) phenyl] borate, or a combination thereof; (b) polyvinyl chloride (PVC); (c) dioctyl sebacate (DOS), 1-nitro-2-(n-octyloxy) benzene (NPOE), or a combination thereof; (d) one or more compounds of formula (I) or formula (II), and (e) carbon. In certain of these embodiments, the ion-selective composition is prepared from a mixture comprising tetraphenylborate, PVC, DOS, Vulcan carbon powder, and one or more compounds of formula (I) or (II).

Representative Cu (II) selective membrane components of the disclosure can be used in the electrodes illustrated in FIGS. 17A-17C. A representative liquid contact ion-selective electrode is shown in FIG. 17A. Referring to FIG. 17A, ISE 100 includes inner reference electrode 110 in liquid contact with inner solution 120 as back contact, and ion-selective membrane 130 (typically polymer based). Representative solid contact ion-selective electrodes are shown in FIGS. 17B and 17C. FIG. 17B shows a solid contact ISE with an insulting membrane. Referring to FIG. 17B, ISE 200 includes electrode 210 (gold, platinum, glassy carbon—as separate alternatives), conductive polymer layer 220 (prepared from representative polymers as polythiophenes, poly (3,4-ethylenedioxythiophene)s, poly(pyrrole)s, and polyanilines) surrounding electrode 210, and ion-selective membrane 230 (typically polymer based). FIG. 17C shows a solid contact ISE with a conductive membrane. Referring to FIG. 17C, ISE 300 includes electrode 310 (copper wire), carbon layer 320 surrounding electrode 310, and ion-selective membrane 330 (carbon-based). In these representative ISEs, the ion-selective membrane includes a Cu (II) ionophore compound of the disclosure (e.g., one or more compounds of formula (I) or (II)).

In some embodiments, the selectivity coefficients of this $Cu^{2+}$ microsensor are log $K_{Cu^{2+}, A}$=-2.13, -3.80, -3.15, -3.42, -3.09, -2.55, -3.10, -3.00, and -2.21 for $H^+$, $Na^+$, $K^+$, $Mg^{2+}$, $Ca^{2+}$, $Fe^{2+}$, $Co^{2+}$, $Zn^{2+}$, and $Pb^{2+}$, respectively. The presence of hydrophobic dendritic moiety in the compounds of the disclosure makes them less prone to leaching from a hydrophobic membrane in an aqueous matrix, while the cinnamaldehyde component of the molecule helps in the detection of $Cu^{2+}$ ions fluorometrically, as indicated by a change in fluorescence upon selective and reversible binding of the molecular probe to the $Cu^{2+}$ ions. The strategic design of the molecular probe allows us to detect $Cu^{2+}$ ions in drinking water by using the Cu (II) solid-state microsensor.

In another aspect, the disclosure provides a colorimetric device comprising a membrane impregnated with one or more compounds of formula (I) or (II). In some embodiments, the membrane is a cellulose membrane. In some embodiments, the colorimetric device is disposable. In some embodiments, the colorimetric device is a device that can be used for water testing (e.g., a test strip for testing tap water for the presence of Cu(II)).

The following is a description of representative Cu (II) ionophore compounds, their compositions (e.g., ionophore-containing membranes), and sensors (e.g., ion-selective electrodes) and their use in potentiometric, fluorometric, and colorimetric determination of Cu (II) ions.

Figure 2A:
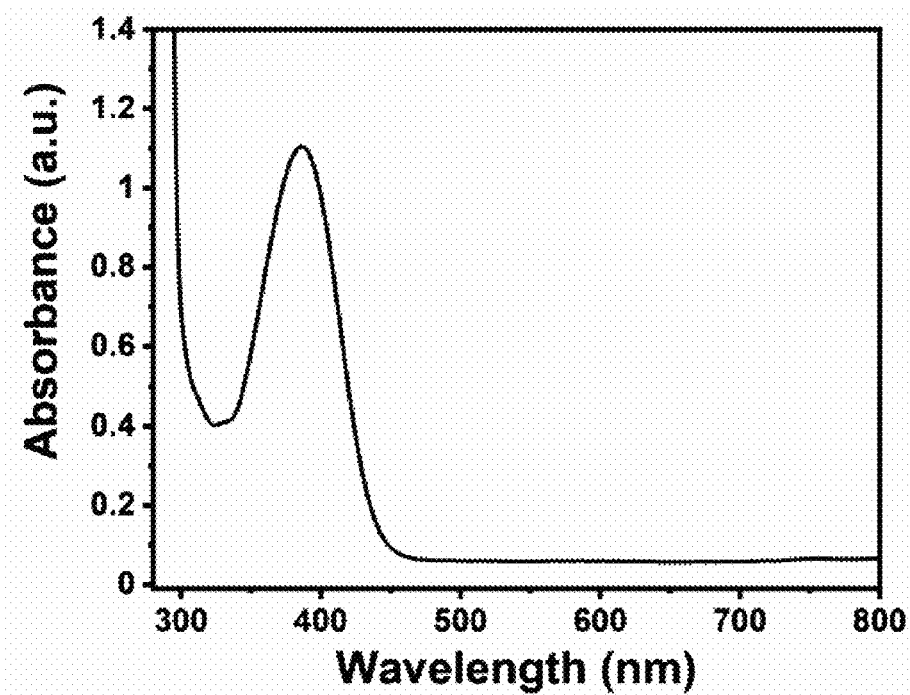
FIGS. 2A-2C show UV-Vis characterization of metal-ligand binding: UV-Vis spectra of the exemplary compound ($2\times10^{-5}$ M) with an absorption maximum centered at 387 nm (2A); Job's plot indicates that the ligand-to-metal binding ratio is 1:1 (number of experiments=3) (2B); and the Benesi-Hildebrand plot provides a binding constant of the complexation ($3.51\times10^5$ $M^{-1}$) (number of experiments=3) (2C).
Figure 2B:
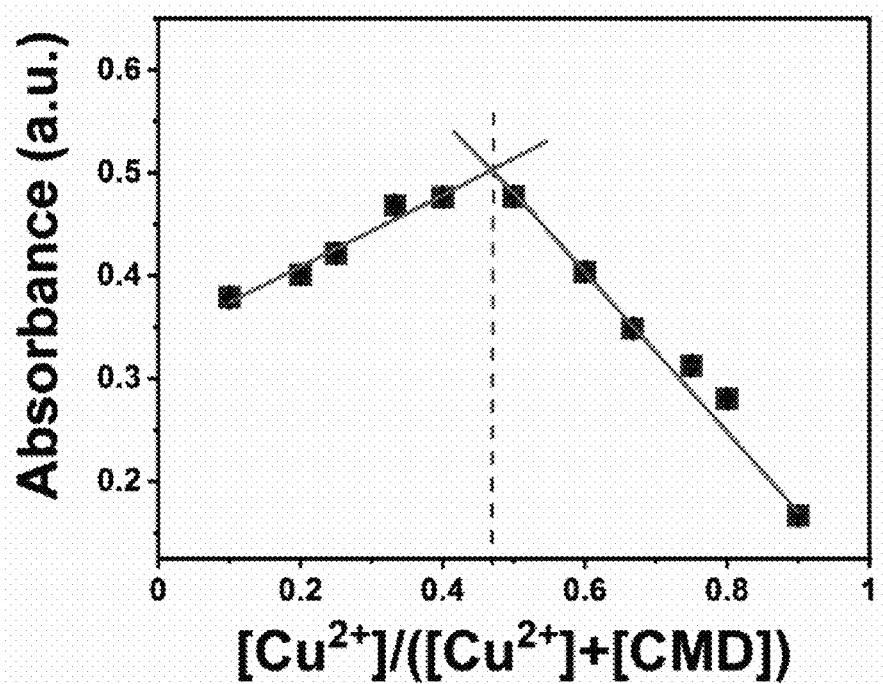
Figure 2C:
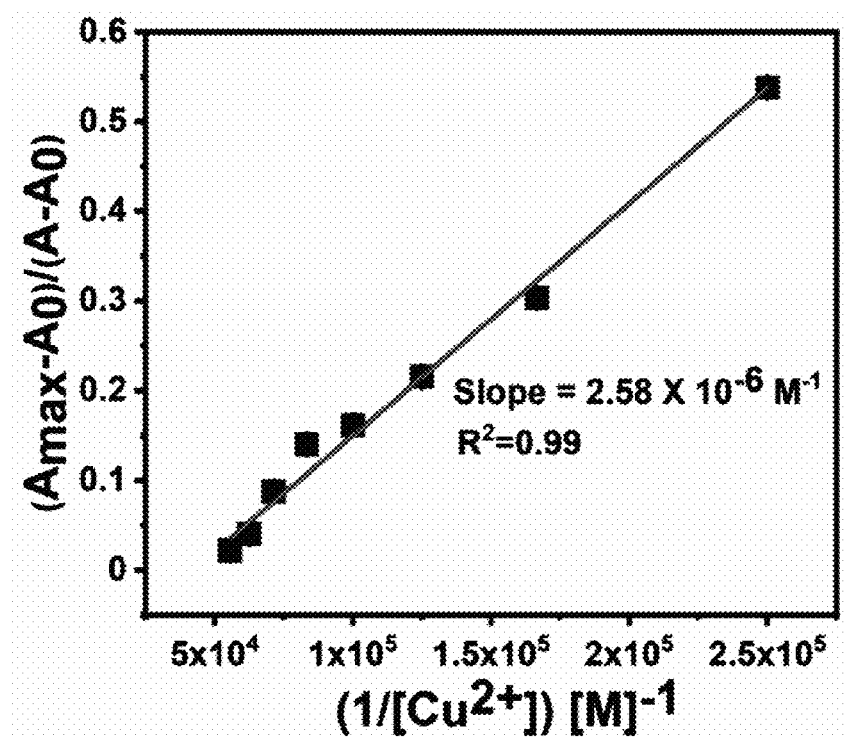
Figure 3A:
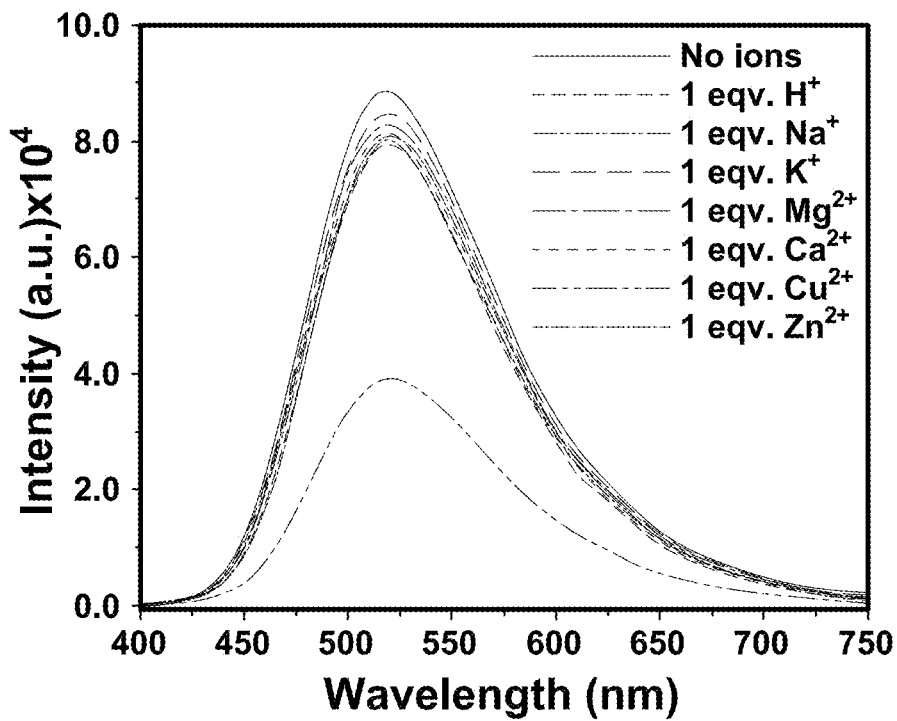
FIGS. 3A-3C show fluorescence characterization of the exemplary cinnamaldehyde modified dendron (CMD)-metal complex: Fluorescence spectra of the exemplary compound in the presence of different metal ions, excitation wavelength 387 nm (3A); interference test against metal ions (number of experiments=3) (3B); and fluorescence calibration for $Cu^{2+}$ ion to find the sensitivity and detection limit of the $Cu^{2+}$ ion quantification (number of experiments=3) (3C).
Figure 3B:
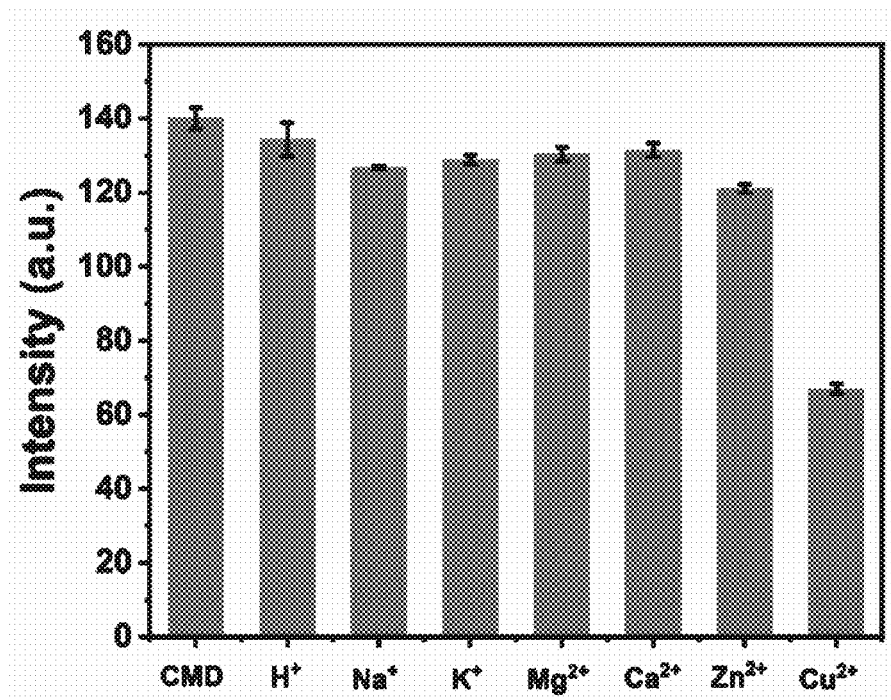
Figure 3C:
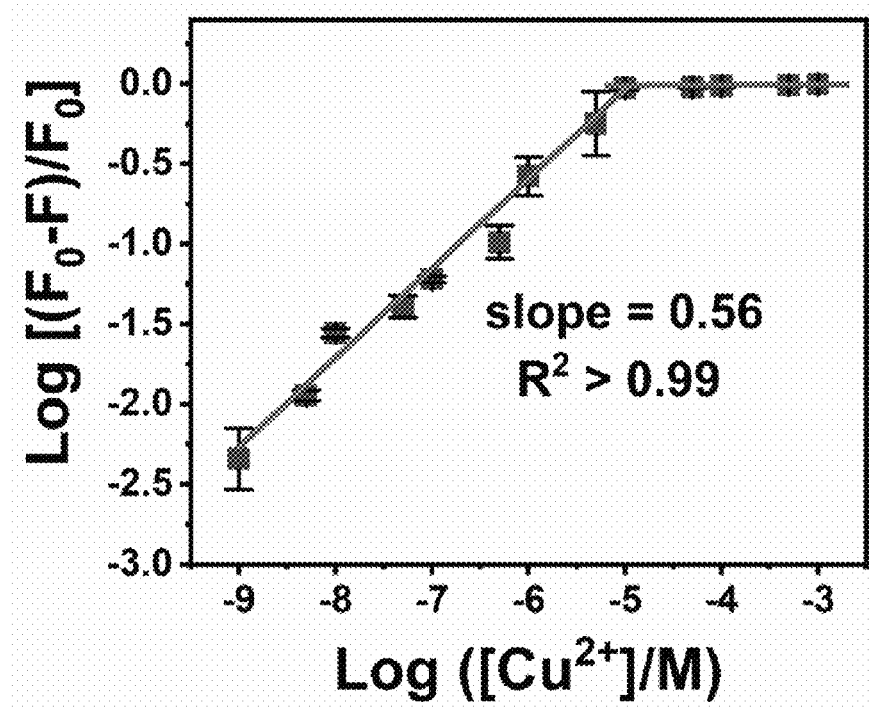

Molecular Design of a Representative Cu (II) Ionophore and Fluorometric Characterization The disclosed design for a representative molecular probe (Cu (II) ionophore compound of formula (II) shown in FIG. 1), with the cinnamaldehyde component, a fluorogenic center, along with a benzo hydrazide moiety to bind with $Cu^{2+}$, allows detection of Cu (II) fluorometrically. The UV-Vis spectrum of the Cu (II) ionophore compound of formula (II) was obtained and showed the absorption band with the absorption maximum centered at 387 nm, which is characteristic of the cinnamaldehyde component of the molecule (FIG. 2A). The ligand-to-metal binding stoichiometry was obtained from the Job's plot. The data indicate that the ligand-to-metal binding ratio is 1:1 (FIG. 2B). The slight deviation of the ratio obtained from the Job's plot from 0.5 is possibly due to the changes in the ionic strength of the solution as the concentration of $CuCl_2$ was increased. The Benesi-Hildebrand plot was also obtained to determine the binding constant by considering 1:1 metal-to-ligand binding. The calculated binding constant was $3.51 \times 10^5$ $M^{-1}$ (FIG. 2C). To demonstrate the ability of the CMD molecule ($2 \times 10^{-5}$ M) to detect $Cu^{2+}$ via fluorescence spectroscopy, we characterized the molecule itself by using methanol as a solvent. The CMD was simply used as a fluoroionophore in organic solvents. Methanol was used as a solvent because the dendritic molecular probe is soluble in methanol but not in water. The molecule showed fluorescence emission centered at 520 nm when excited at 387 nm wavelength light (FIG. 3A). For the molecule to act as a molecular probe, it should be highly selective and sensitive toward different metal ions. The selectivity of CMD was tested against different metal ions, including $H^+$, $Na^+$, $K^+$, $Mg^{2+}$, $Ca^{2+}$, $Cu^{2+}$, and $Zn^{2+}$ (FIG. 3B). Significant selective fluorescence quenching was observed when $Cu^{2+}$ ions were added to the fluorophore. After the addition of various known concentrations of $Cu^{2+}$ ions, a calibration curve was obtained that suggested the use the molecule as a fluorescent molecular probe to detect and quantify $Cu^{2+}$. The detection limit was calculated to be 15 nM (S/N=3) (FIG. 3C), which is better than the other fluorescence quenching based $Cu^{2+}$ ion-selective sensors reported by Estrella et al. (5.6 µM), Weng et al. (1.5 µM), Rahimi et al. (3 µM), and Kim et al. (0.38 µM) (E. Espada-Bellido, M. D. Galindo-RIANO, M. Garcia-Vargas, R. Narayanaswamy, Selective chemosensor for copper ions based on fluorescence quenching of a schiff-base fluorophore, *Appl. Spectrosc.* 64 (2010) 727-732; Y. Q. Weng, Y. L. Teng, F. Yue, Y. R. Zhong, B. H. Ye, A new selective fluorescent chemosensor for Cu (II) ion based on zinc porphyrin-dipyridylamino, *Inorg. Chem. Commun.* 10 (2007) 443-446; Y. Rahimi, S. Shrestha, S. K. Deo, Metal affinity-based purification of a red fluorescent protein, *Chromatographia* 65 (2007) 429-433; and H. S. Kim, H. S. Choi, Spectrofluorimetric determination of copper (II) by its static quenching effect on the fluorescence of 4,5-dihydroxy-1,3-benzenedisulfonic acid, *Talanta* 55 (2001) 163-169).

Figure 4A:
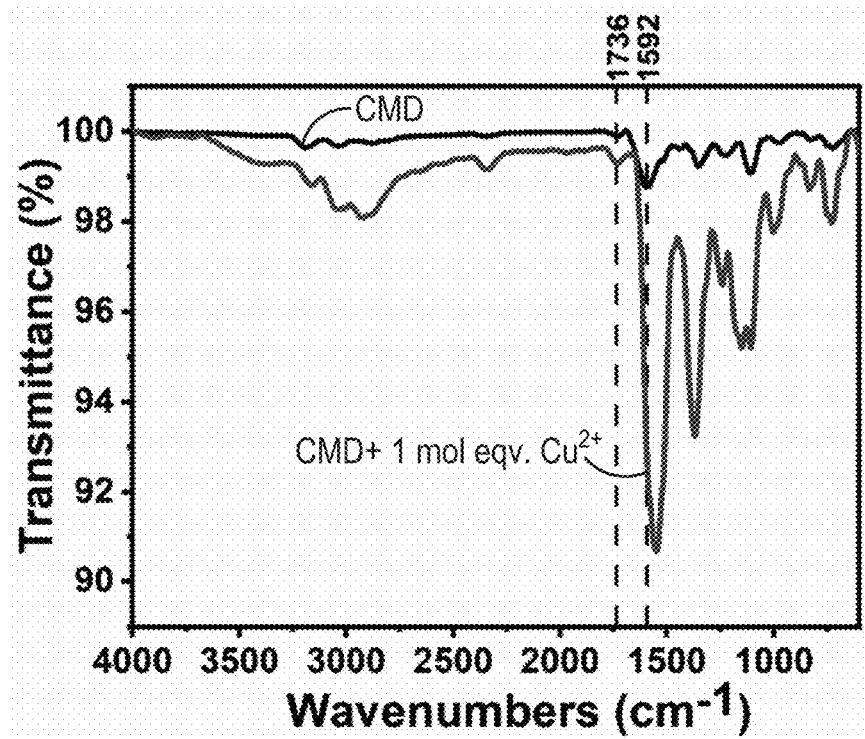
FIGS. 4A and 4B show possible mechanisms of $Cu^{2+}$ binding: FT-IR spectra of the exemplary cinnamaldehyde modified dendron ionophore before and after the addition of 1 mol eqv. $Cu^{2+}$ (4A); possible $Cu^{2+}$ binding site of the ionophore (4B).
Figure 4B:
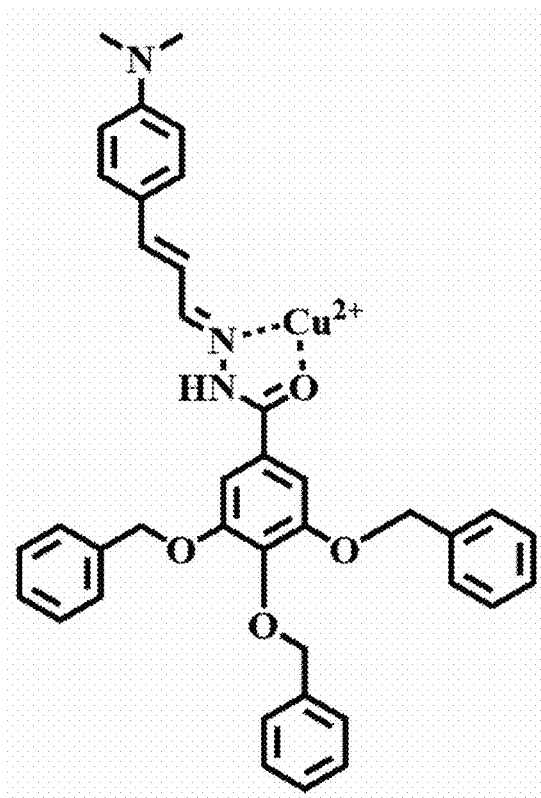

To gain additional insights into the binding mode in the CMD-$Cu^{2+}$ complex, the FT-IR spectra of the free CMD (1 mM) and CMD-$Cu^{2+}$ (1:1) complex in methanol were obtained (FIGS. 4A and 4B). The characteristic $\upsilon$(C=O) stretching vibrational mode appeared at 1736 $cm^{-1}$, and the $\upsilon$(C=N) stretching vibrational mode appeared at 1592 $cm^{-1}$ in CMD, which shows a downward shift of 10 and 42 $cm^{-1}$, respectively, in the complex form, indicating that the carbonyl oxygen and the imine nitrogen of the CMD are involved in binding. Therefore, CMD acts as a bidentate ligand while complexing with the $Cu^{2+}$ ion.

Potentiometric Characterization of a Representative Cu (II) Ionophore

Figure 5A:
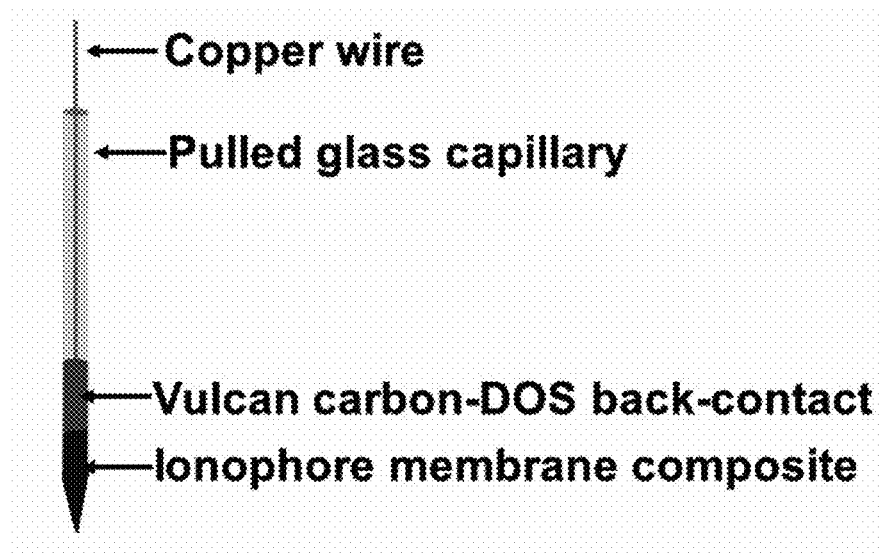
FIGS. 5A and 5B show potentiometric characterization of the $Cu^{2+}$ ISE: (A) schematic of the carbon-packed Cu (II) microsensor (5A); and potentiometric calibration of $Cu^{2+}$ with the carbon-packed sensor (5B). DOS: dioctyl sebacate. The sensors showed Nernstian slope of 29.3±2.9 mV/log $[a_{Cu^{2+}}]$ and detection limits of 3.5±1.0 µM (number of experiments=6)
Figure 5B:
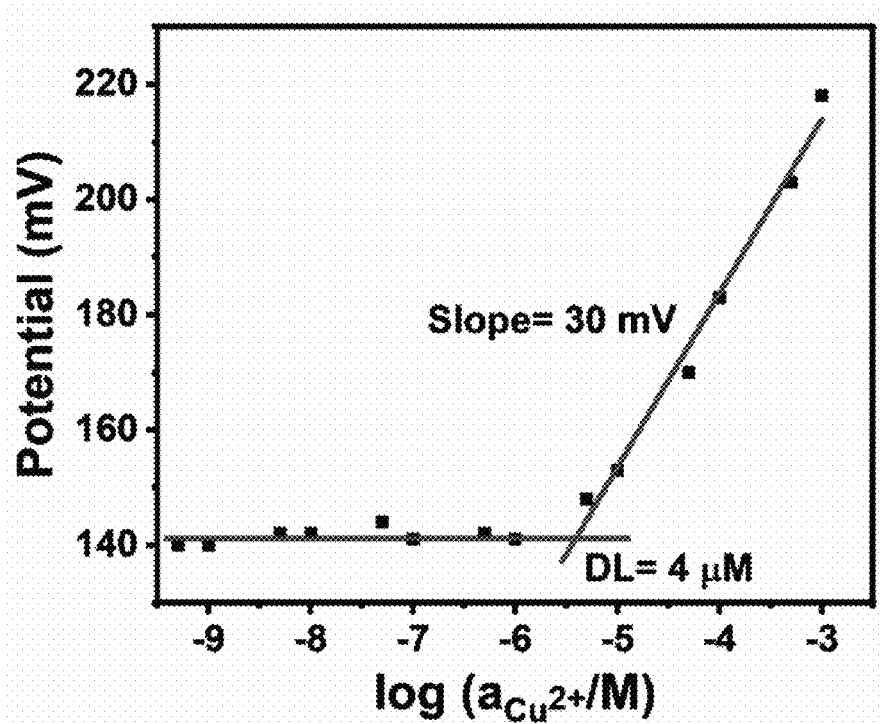
Figure 7:
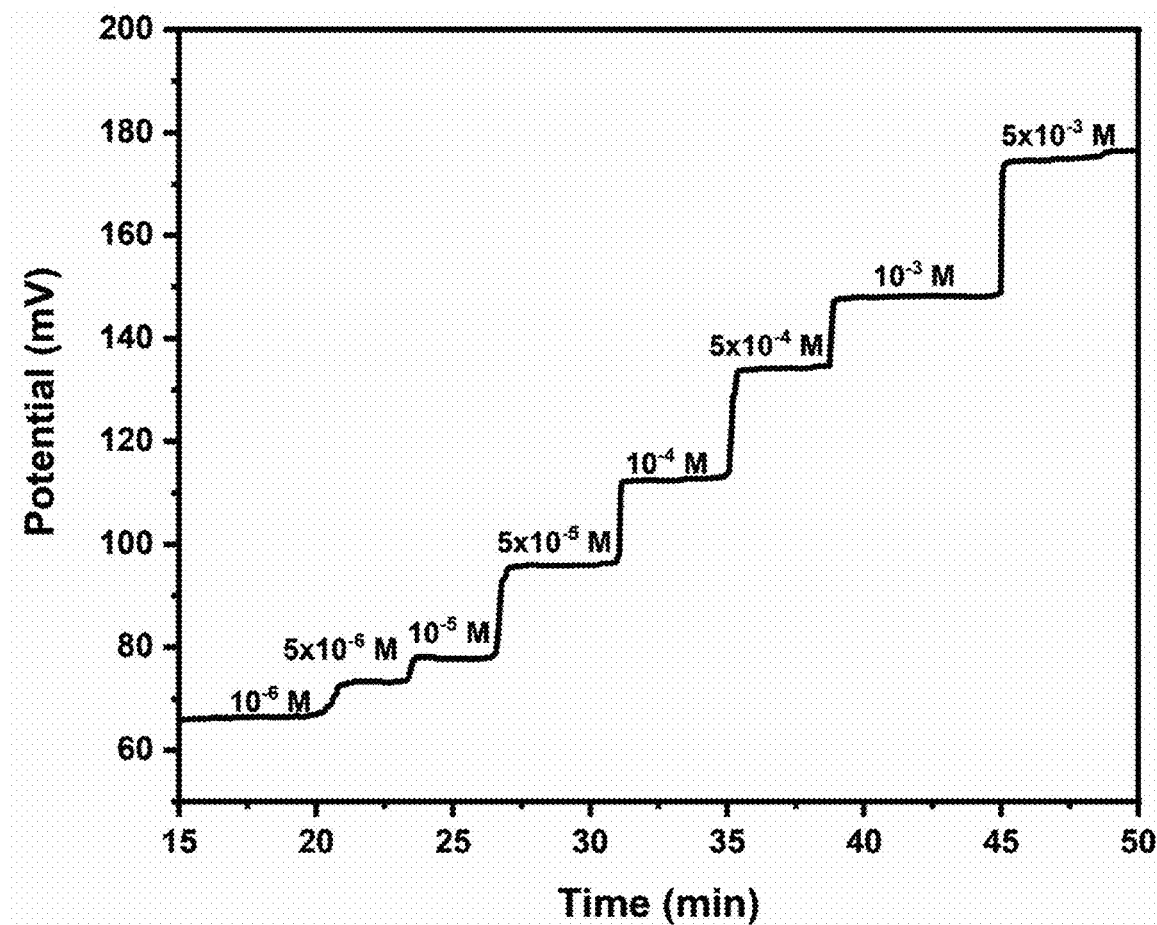
FIG. 7 shows the potential response of the exemplary $Cu^{2+}$ microsensor upon the addition of $Cu^{2+}$ ions.
Figure 8:
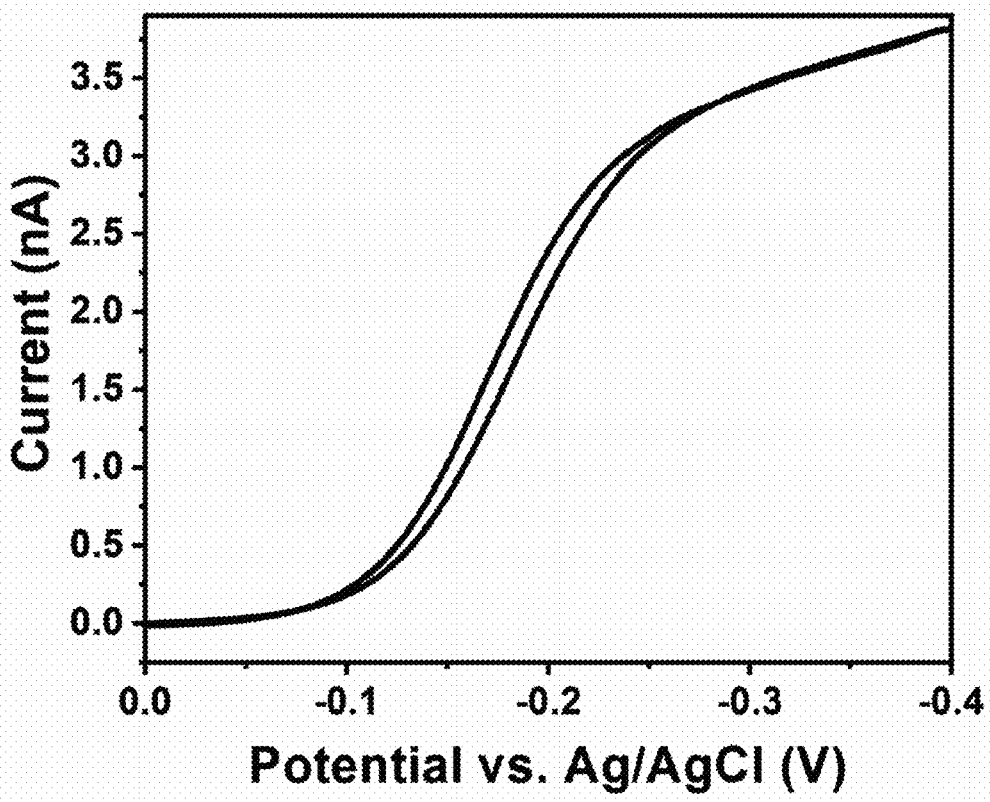
FIG. 8 shows cyclic voltammetry of $Cu^{2+}$ micro-ISE in 1 mM RuHex in 0.1 M KCl (vs Ag/AgCl).

The disclosed Cu (II) ionophore can be used as an ionophore for constructing a solid-state ISE for the detection of Cu (II) via potentiometry. A solid-state micro-ISE was constructed with the CMD as the ionophore, PVC as the binding polymer, a plasticizer, a hydrophobic anion, and Vulcan carbon, which gives a near Nernstian response of 30 mV/log $[a_{Cu^{2+}}]$ (FIGS. 5A and 5B). The characteristic response of the Cu (II) ISE to the addition of $Cu^{2+}$ ion is shown in FIG. 7. The introduction of the Vulcan carbon makes the membrane conductive, potentially allowing it to be used as an amperometric probe, as shown in cyclic voltammetry (FIG. 8). The electroactive surface area of the electrode was calculated using the voltammogram of RuHex. The calculated electroactive surface area suggests that electrode has an electroactive diameter of 23 m even though the geometric diameter of the electrode is 25 m. Unlike a metal electrode, the electroactive surface area of the micro-ISE is less than the geometric surface area, which is probably due to the presence of electro-inactive sites containing polyvinyl chloride (PVC) within the ion-selective membrane. Because of the small size of the micro-ISE, it can be used to measure Cu (II) in a small volume of the sample matrix. The components and their amounts were varied in the ion-selective membrane to optimize the membrane composition (Table 1). The sensors showed Nernstian slope of 29.3±2.9 mV/log $[a_{Cu^{2+}}]$ and detection limits of 3.5±1.0 µM (Table 1). The incorporation of a plasticizer plays a vital role in a PVC-based ISE because it can provide ionic mobility within the membrane. The performance of two different plasticizers, NPOE and DOS, were compared in the membrane. As shown in Table 1, a better slope of the sensor is obtained by incorporating DOS. The performance of the plasticizer usually depends on the dielectric constants and DOS has a relatively lower value of it. A hydrophobic counter anion is often included into the membrane to facilitate cation extraction within the membrane, reduce ohmic resistance, and improve response behavior. Different lipophilic anions, such as KTCPB, NaTFPB, and NaTPB, were compared for the construction of the micro-ISE and found that the slope was worst for NaTFPB. In contrast, NaTPB showed the best response because of its better ion extraction ability and the optimum lipophilic anion to ionophore mole ratio, which was 0.5. TPB is a stronger ion exchanger due to the absence of electronegative halides (has a negative inductive effect), which makes the electron localization on the boron atom leads to a stronger ion-pair formation with the analyte. After investigation of the membrane components, the composition of ISE membrane was optimized as 10% ionophore, 2.8% tetraphenylborate, 3% PVC, 30% DOS, and 54.2% Vulcan carbon, which gives a Nernstian response of 29.3 (±2.9) mV/log $[a_{Cu^{2+}}]$ (linear range 10 µM to 1 mM) with a detection limit of 3.5 (±1.0) µM.

Figures 6A, 6B:
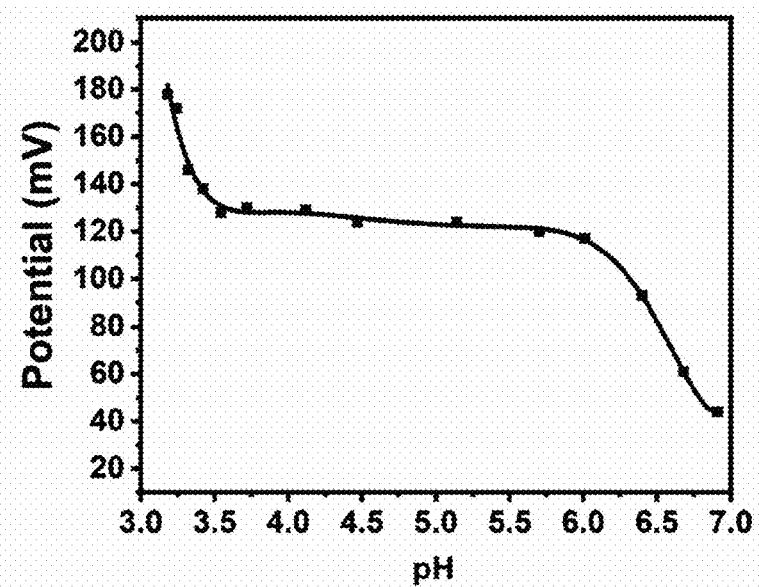
FIG. 6A shows the effect of pH on the carbon-packed sensor using the CMD ionophore.
FIG. 6B is a selectivity table of the carbon-packed sensor using the CMD ionophore is compared against the commercial ionophore, copper (II) ionophore I (L. K. L. Su, Chia-ching, Chuen-Her Ueng, Characteristics of Lariat Crown Ether-Copper (II) Ion-Selective Electrodes, *J. Chinese Chem. Soc.* 48 (2001) 733-738)).
Figure 9:
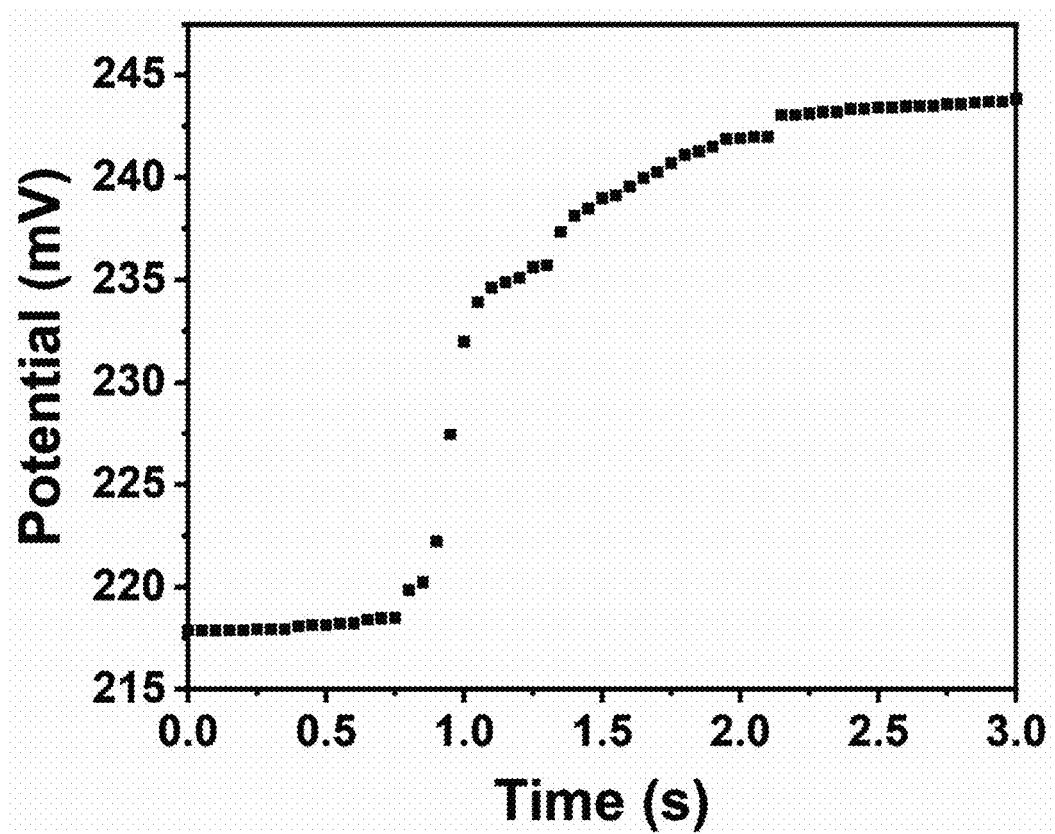
FIG. 9 shows the response time of the exemplary $Cu^{2+}$ microsensor.
Figure 10:
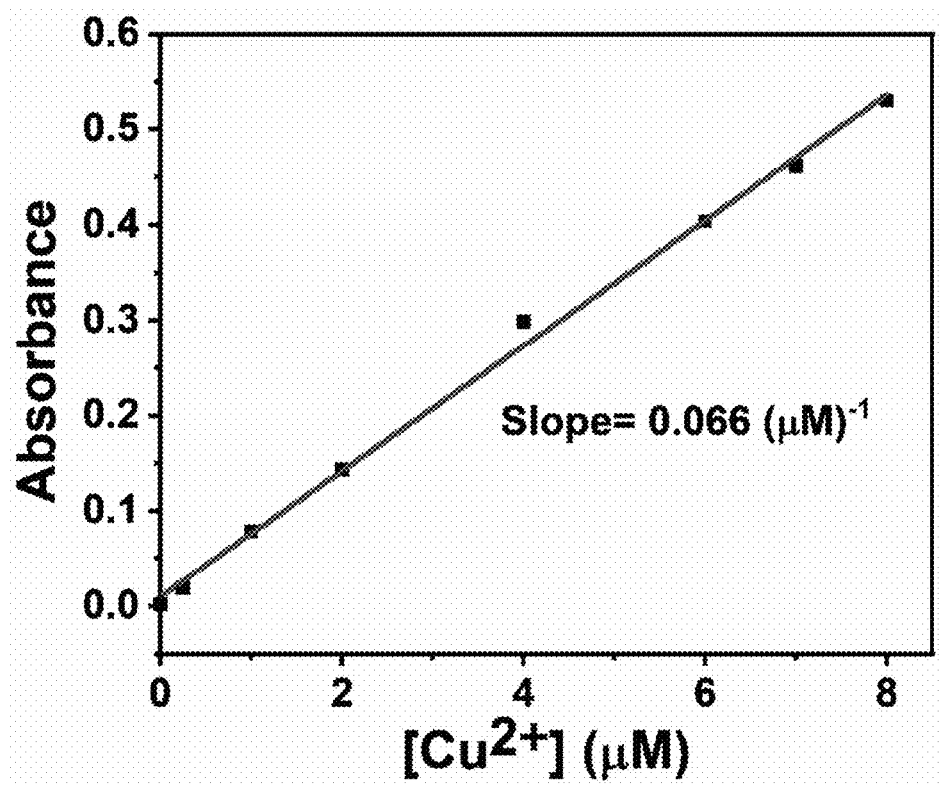
FIG. 10 is a calibration plot for the atomic absorption (AA) spectroscopy.
Figure 15A:
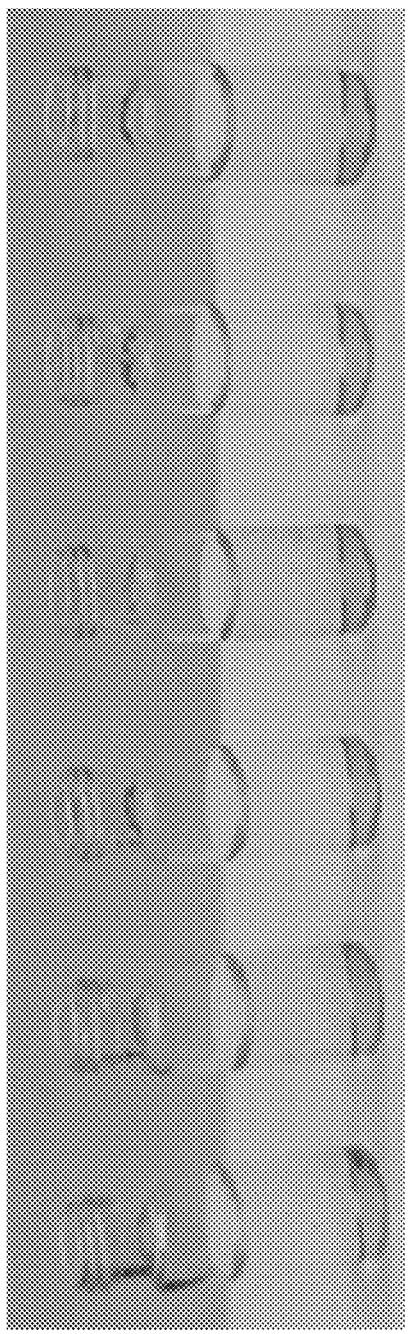
FIG. 15A illustrates visual detection of CMD reversibility under normal and UV light (excitation at 365 nm) (in order: I=20 µM CMD; II=I+5 µM $Cu^{2+}$; III=II+5 µM EDTA; IV=III+5 µM $Cu^{2+}$; V=IV+5 µM EDTA; VI=V+5 µM $Cu^{2+}$)
Figure 15A:
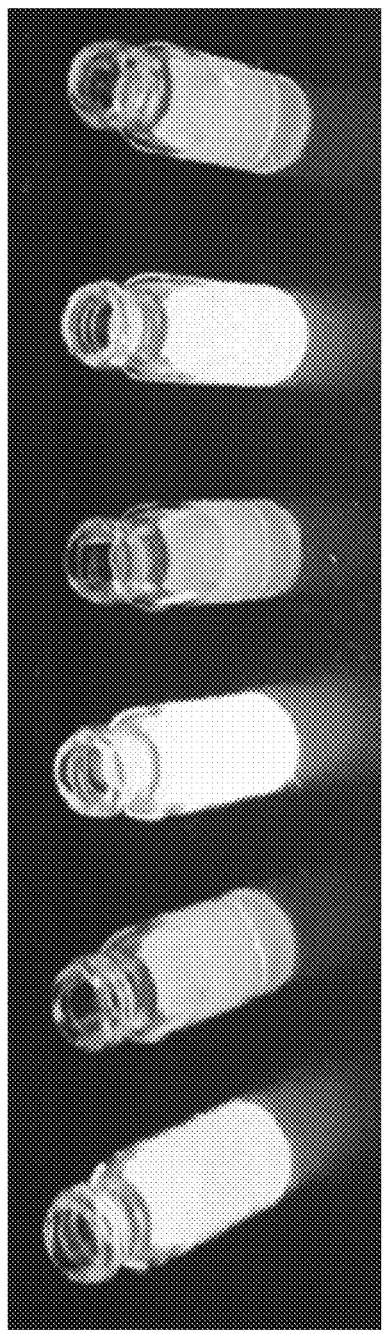
Figure 15B:
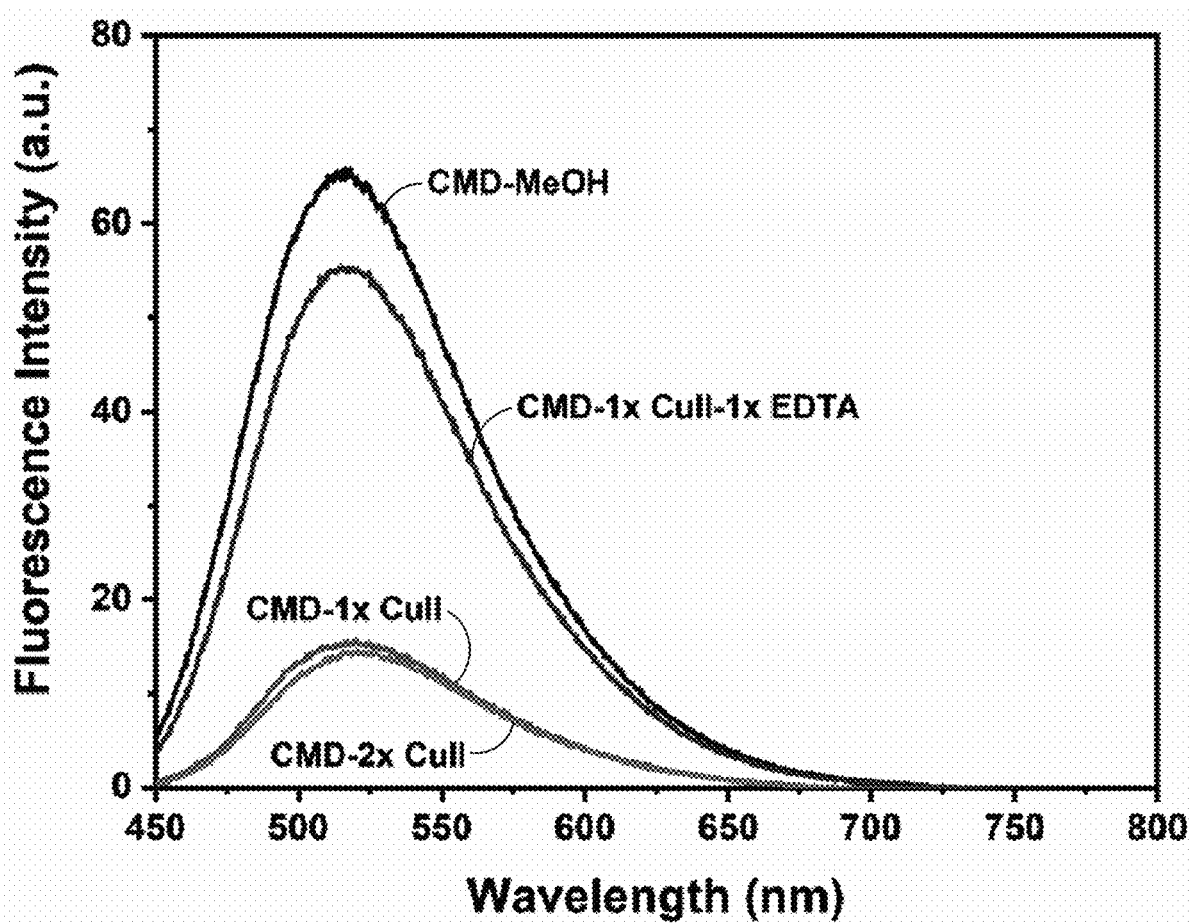
FIG. 15B compares fluorescence spectra of CMD reversibility performed with alternate additions of 5 µM $Cu^{2+}$ and 5 µM EDTA in 20 µM CMD.
Figure 15C:
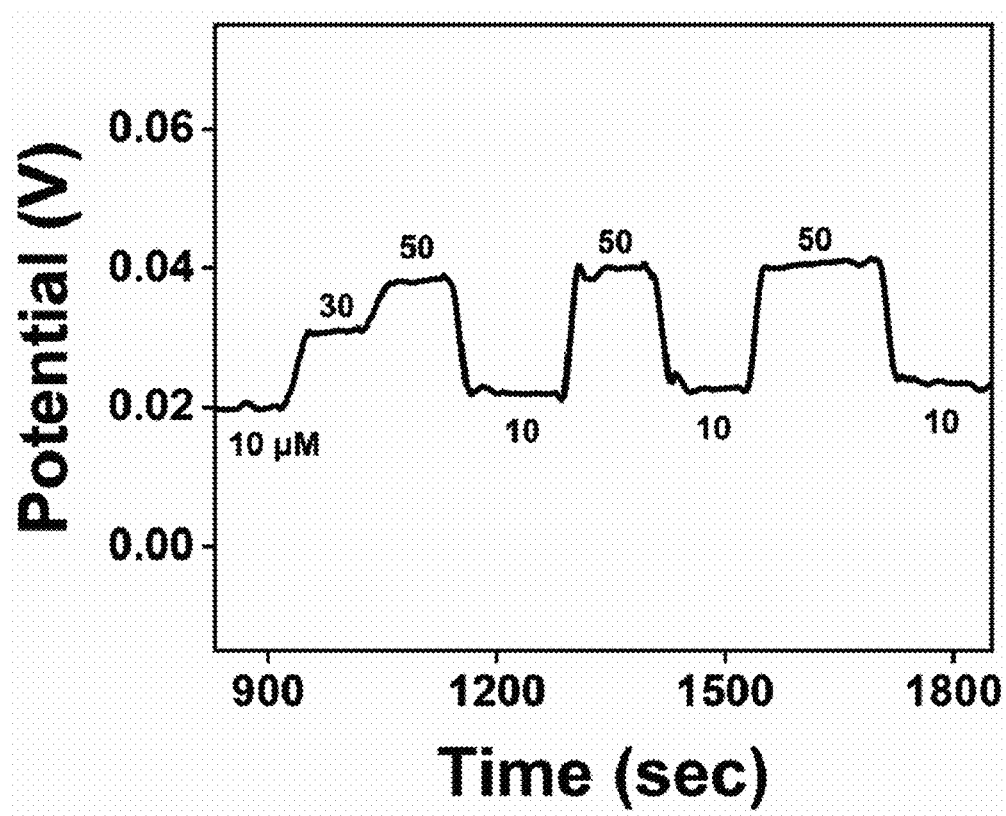
FIG. 15C illustrates the reversibility of $Cu^{2+}$-ISE. The potential was recorded while the $Cu^{2+}$ concentration was repeatedly changed from 10 µM to 50 µM and vice versa.

The selectivity values for most of the metal ions were found to be $\leq -3$, which is an improvement of almost one order of magnitude over the commercially available Cu (II) ionophore-I (S. Kamata, H. Murata, Y. Kubo, A. Bhale, Copper (ii)-selective membrane electrodes based on o-xylylene bis (dithiocarbamates) as Neutral Carriers, *Analyst* 114 (1989) 1029-1031) (FIG. 6B). The sensor was also compared with the sensor containing commercially available Cu (II) ionophore I in terms of detection limit, slope, response time, and pH range (Table 2). FIG. 9 represents a response time of 1.5 s obtained from the Cu (II) ISE. The reversibility of the sensors was carefully investigated using potentiometric and fluorometric techniques. The reversibility of the Cu (II) sensor was demonstrated using both techniques in FIGS. 15A-15C. The ionophore shows reversible behavior in both potentiometric and fluorometric modes.

TABLE 1

Composition and characterization of carbon-packed sensors, including slope, linear range, and detection limit (number of experiments = 6).

| I (%) | LA (%) | Plasticizer (%) | PVC (%) | VC (%) | Molar ratio (LA:I) | Linear range (M) | Slope (mV/log $[a_{Cu}^{2+}]$) | DL (µM) |
|---|---|---|---|---|---|---|---|---|
| 6.9 | KTCPB (2.0) | NPOE (30) | 3 | 58.1 | 0.3 | $10^{-5}$-$10^{-3}$ | 11.8 ± 4.2 | 13.8 ± 1.8 |
| 6.9 | KTCPB (3.3) | NPOE (30) | 3 | 56.8 | 0.6 | $10^{-5}$-$10^{-3}$ | 12.5 ± 1.3 | 11.1 ± 0.8 |
| 6.9 | KTCPB (1.4) | DOS (30) | 3 | 56.8 | 0.2 | $10^{-5}$-$10^{-3}$ | 14.8 ± 2.5 | 10.0 ± 3.3 |
| 6.9 | KTCPB (3.3) | DOS (30) | 3 | 56.8 | 0.6 | $10^{-5}$-$10^{-3}$ | 17.2 ± 3.0 | 7.8 ± 2.2 |
| 10 | KTCPB (3.5) | DOS (30) | 3 | 53.5 | 0.4 | $10^{-5}$-$10^{-3}$ | 16.0 ± 1.0 | 9.6 ± 0.9 |
| 10 | KTCPB (4.5) | DOS (30) | 3 | 52.5 | 0.6 | $10^{-5}$-$10^{-3}$ | 19.4 ± 0.5 | 16.2 ± 2.5 |
| 10 | NaTFPB (6.0) | DOS (30) | 3 | 51.0 | 0.4 | $10^{-5}$-$10^{-3}$ | 15.0 ± 3.6 | 334.1 ± 105.8 |
| 7 | NaTPB (2.0) | DOS (30) | 3 | 58.0 | 0.5 | $10^{-5}$-$10^{-3}$ | 7.1 ± 2.8 | 54.2 ± 34.7 |
| 10 | NaTPB (1.4) | DOS (30) | 3 | 55.6 | 0.3 | $10^{-5}$-$10^{-3}$ | 23.6 ± 7.2 | 3.0 ± 1.0 |
| 10 | NaTPB (2.8) | DOS (30) | 3 | 54.2 | 0.5 | $10^{-5}$-$10^{-3}$ | 29.3 ± 2.9 | 3.5 ± 1.0 |

I: ionophore; LA: lipophilic anion; PVC: polyvinyl chloride; VC: vinyl chloride; DL: detection limit; KTCPB: potassium tetrakis(4-chlorophenyl) borate; NaTFPB: sodium tetrakis [3,4-bis(trifluoromethyl) phenyl] borate; NaTPB: sodium tetraphenylborate; NPOE: 1-nitro-2-(n-octyloxy) benzene; DOS: dioctyl sebacate.

The effect of pH on the sensor was measured in the presence of $10^{-3}$ M CuCl$_2$. The pH of the solution was adjusted by using either 0.1 M HCl or 0.1 M NaOH. FIG. 6A shows the effect of pH on the response in potential by the Cu (II) microsensor. The potential remains constant within the pH range from 3.5 to 6.0 for the microsensor. The response in potential outside this range is due to interference by H$^+$ at the low end of the pH scale and Cu(OH)$_2$ formation at the higher end of the pH scale. Therefore, the working pH range for the present electrode is from 3.5 to 6.0. The activity was obtained by only considering the presence of Cu$^{2+}$ and Cl$^-$ in the system. Formation of complexes like Cu(OH)$^+$ and CuCl$^+$ was not taken into account because the working pH range for the ISE is from 3.5 to 6.0, and within this pH range, the aqueous solution of CuCl$_2$ exists primarily as Cu$^{2+}$ and Cl$^-$. The selectivity test was performed with different metal ions such as H$^+$, Na$^+$, K$^+$, Mg$^{2+}$, Ca$^{2+}$, Fe$^{2+}$, Co$^{2+}$, Zn$^{2+}$, and Pb$^{2+}$. The ion-selective membrane electrode shows high selectivity toward Cu$^{2+}$ ions and the selectivity coefficients were calculated as log $K_{Cu^{2+}, A}\leq$ −2.13, −3.80, −3.15, −3.42, −3.09, −2.55, −3.10, −3.00, and −2.21, respectively.

TABLE 2

Comparison table for the sensing performance between the ISEs made with CMD as ionophore vs. ISEs containing the commercially available Cu (II) ionophore I.

| Parameters | CMD | Cu (II) ionophore I |
|---|---|---|
| Detection limit (µM) | 3.5 | 0.14 |
| Slope (mV/decade) | 29.3 | 29 |
| Response time (s) | 1.5 | 9 |
| pH range | 3.5-6.0 | 3.2-5.5 |

Detection of Cu$^{2+}$ in Tap Water

Figure 16:
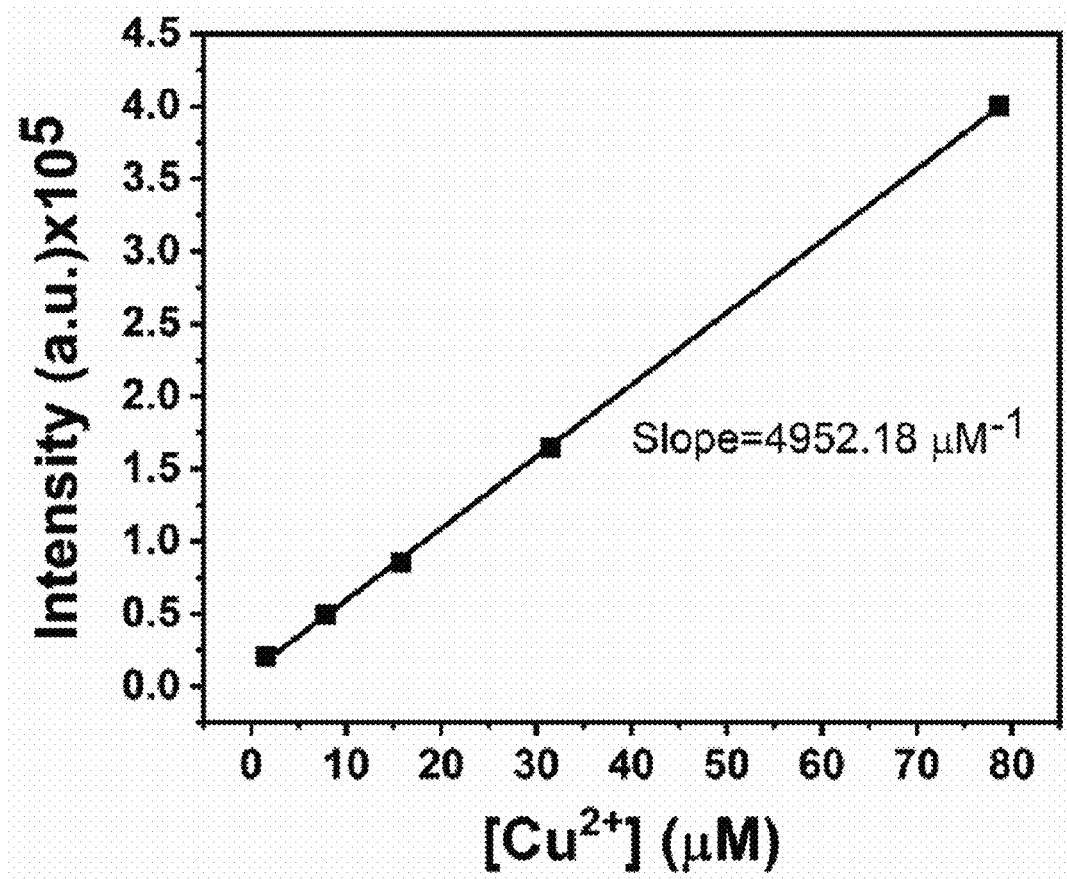
FIG. 16 is a calibration plot for the inductively coupled plasma-optical emission spectrometry (ICP-OES).

The Cu (II) micro-ISE was used to measure the amount of copper present in tap water collected from the main campus of Oregon State University (OSU). The CMD ionophore was also used as a fluorometric Cu (II) sensor to measure the amount of Cu$^{2+}$ in the same tap water sample. Further, the results of the quantitative analysis were compared with those of inductively coupled plasma-optical emission spectrometry (ICP-OES) as a standard technique (Table 2). The calibration plot obtained with ICP-OES is shown in FIG. 16. The amount of Cu (II) present in OSU campus (Gilbert Addition) tap water was found to be 38.0±1.7 µM using ISE, 38.9±0.9 µM using fluorimetry, and 38.0±0.9 µM from ICP-OES. This indicates that the amount of copper present in water samples can be determined by using the CMD fluoroionophore. The agreement of $Cu^{2+}$ concentrations obtained from three different methods also suggests that contribution from complexes is minimal by acidification of tap water samples.

TABLE 3

Water samples were collected, and the amount of $Cu^{2+}$ was found in samples by using a $Cu^{2+}$ ion-selective electrode (ISE) and atomic absorption spectroscopy (AAS) (number of experiments = 3).

| Water Sample | ISE | Fluorimetry | ICP-OES |
|---|---|---|---|
| Tap water (Gilbert Hall Addition at Oregon State University) | 38.0 ± 1.7 µM | 38.9 ± 0.9 µM | 38.0 ± 0.9 µM |

Paper-Based Colorimetric $Cu^{2+}$ Sensor Using Cinnamaldehyde Modified Dendron Molecule (CMD)

Colorimetric detection of copper ion was investigated using cinnamaldehyde modified dendron molecule compound of formula (II) (CMD). The color change of CMD solutions was observed by dissolving 5 mg of CMD in 0.150 mL of DMF followed by the addition of 0.850 mL of aqueous $Cu^{2+}$ ion (different concentrations from 1 µM to 1 mM). A distinct color change was observed from green to yellow to orange to red. Table 4 shows the results of the hydrogelation test with cinnamaldehyde modified dendron (CMD).

TABLE 4

Hydrogelation Test.

| Gelator (mg) | DMF (mL) | Other components (mL) | Other components | Observed Color |
|---|---|---|---|---|
| 5 | 0.150 | 0.850 | 1 mM $CuCl_2$ | Green |
| 5 | 0.150 | 0.850 | 10 mM $CuCl_2$ | Light yellow |
| 5 | 0.150 | 0.850 | 100 mM $CuCl_2$ | Yellow |
| 5 | 0.150 | 0.850 | 1 mM $CuCl_2$ | Light Orange |
| 5 | 0.150 | 0.850 | 10 mM $CuCl_2$ | Orange |
| 5 | 0.150 | 0.850 | 100 mM $CuCl_2$ | Light red |
| 5 | 0.150 | 0.850 | 1M $CuCl_2$ | Red |

Figure 11:
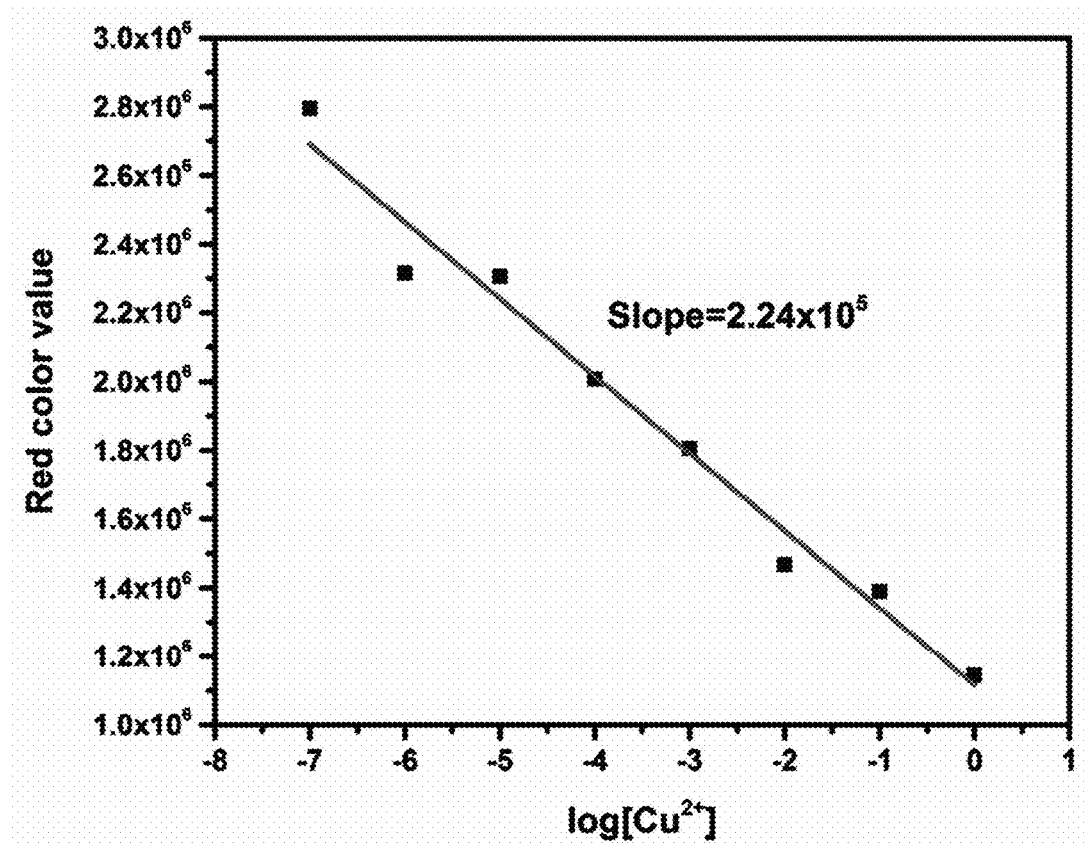
FIG. 11 is a copper ion calibration which was obtained using the red color intensity value obtained using ImageJ software and was plotted against log $[Cu^{2+}]$; with a linear range from 0.1 µM to 1M and slope of $2.24\times10^5$.
Figure 12:
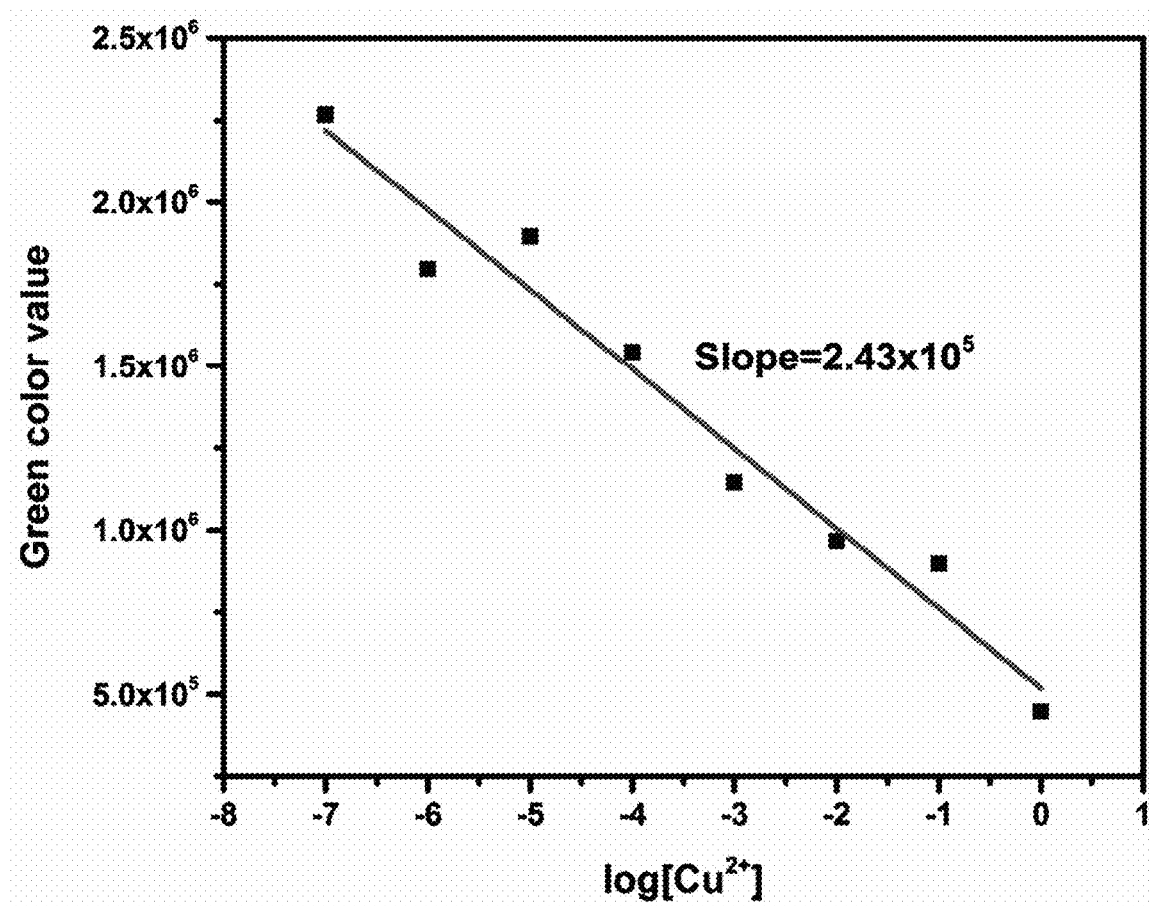
FIG. 12 is a copper ion calibration which was obtained using the green color intensity value obtained using ImageJ software and was plotted against log $[Cu^{2+}]$; with a linear range from 0.1 µM to 1M and slope of $2.43\times10^5$.
Figure 13:
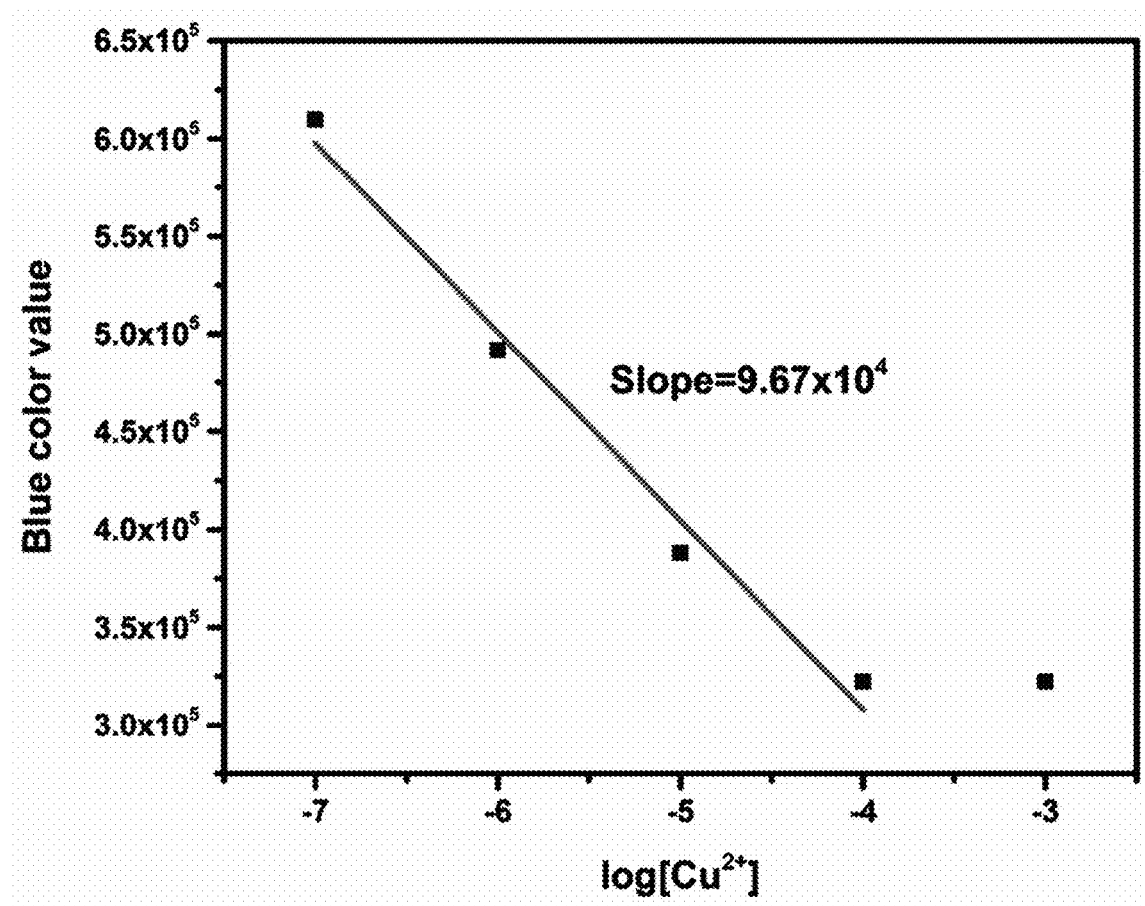
FIG. 13 is a copper ion calibration which was obtained using the blue color intensity value obtained using ImageJ software and was plotted against log $[Cu^{2+}]$; with a linear range from 0.1 µM to 0.1 mM and slope of $9.67\times10^4$.
Figure 14:
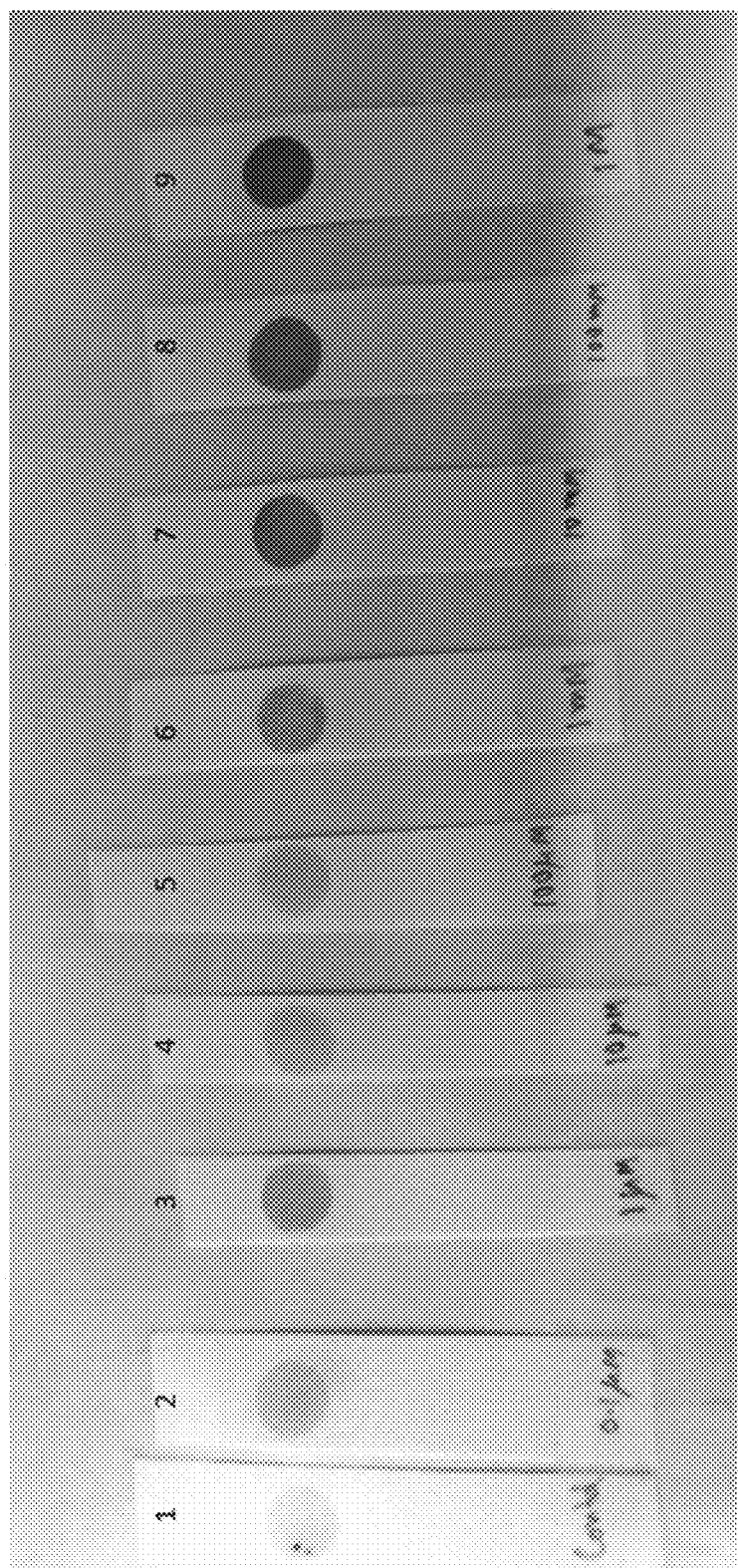
FIG. 14 compares colors of cinnamaldehyde modified dendron (CMD) (1.5 µL of 54.5 mM CMD) drop casted on the Whatman #1 filter paper treated with different concentrations of aqueous solutions of $Cu^{2+}$ ions ($CuCl_2$) were drop casted on the paper.

The CMD molecule can be used to make a paper-based colorimetric device. The color change of CMD-containing paper by drop-casting 1.5 µL of 55 mM CMD (in DMF) on several Whatman #1 filter paper and on top of those drop-casted spots, 1.5 µL of different concentrations of aqueous solutions of $Cu^{2+}$ ions ($CuCl_2$) were drop-casted. A distinct color change was observed when different concentrations of copper ion was added. After the addition of copper to the CMD drop casted filter paper, the final color of the paper was photographed and analyzed using ImageJ software. Using ImageJ, the colored picture was split into Red, Green, and Blue channels, and the respective intensity value was analyzed and plotted against log[$Cu^{2+}$] to obtain a calibration curve for $Cu^{2+}$. Using this method, an unknown concentration of $Cu^{2+}$ ion can be detected. [#1-9:0 µM (control experiment), 0.1 µM, 1 µM, 10 uM, 100 µM, 1 mM, 10 mM, 100 mM, 1 M]. Referring to FIG. 11, a copper ion calibration was obtained using the red color intensity value obtained using ImageJ software and was plotted against log [$Cu^{2+}$] with a linear range from 0.1 µM to 1 M and slope of $2.24 \times 10^5$. Referring to FIG. 12, a copper ion calibration was obtained using the green color intensity value obtained using ImageJ software and was plotted against log [$Cu^{2+}$] with a linear range from 0.1 µM to 1M and slope of $2.43 \times 10^5$. Referring to FIG. 13, a copper ion calibration was obtained using the blue color intensity value obtained using ImageJ software and was plotted against log [$Cu^{2+}$] with a linear range from 0.1 µM to 0.1 mM and slope of $9.67 \times 10^4$. FIG. 14 compares colors of drop cast cinnamaldehyde modified dendron (CMD) on paper when treated with different concentrations of aqueous solutions of $Cu^{2+}$ ions ($CuCl_2$).

As used herein, the terms "$Cu^{2+}$ ions" and "Cu (II) ions" are used interchangeably.

As used herein, the term "about" indicates that the subject value can be modified by plus or minus 5% and still fall within the disclosed embodiment.

All publications cited herein and the subject matter for which they are cited are hereby specifically incorporated by reference in their entireties.

The following examples are provided for the purpose of illustrating, not limiting, the invention. The examples demonstrate the design and synthesis of an exemplary molecular probe to detect Cu (II) by using both potentiometric and fluorometric methods. With the fluorometric technique, up to 15 nM $Cu^{2+}$ could be detected, and the compound shows selectivity toward $Cu^{2+}$ ions when tested against common metal ions such as $H^+$, $Na^+$, $K^+$, $Ca^{2+}$, $Mg^{2+}$, and $Zn^{2+}$. The molecular probe was used as an ionophore to develop a carbon-based solid-state micro-ISE to detect Cu (II) in a drinking water sample. The selectivity of the ionophore represents an improvement of at least one order of magnitude over the commercial ionophore and has a fast response time (1.5 s). With its improved selectivity and response time, this exemplary microsensor can be used to detect Cu (II) ions in micro-volumes, which also makes it compatible with scanning electrochemical microscopy (SECM).

Examples

The following examples describe the preparation of an exemplary Cu (II) ionophore compound useful as a dual probe for potentiometry and fluorimetry that allows quantification of Cu (II) ion concentration by using a single multifunctional molecule instead of two different molecules for potentiometry and fluorimetry separately.

Materials

All starting materials for the synthesis of cinnamaldehyde modified dendron (CMD) were obtained from Sigma-Aldrich. Vulcan carbon was obtained from Cabot Corporation. PVC was purchased from Aldrich. Tetramethyl silane was purchased from CIL. Potassium tetrakis(4-chlorophenyl) borate (KTCPB), sodium tetrakis [3,4-bis(trifluoromethyl) phenyl] borate (NaTFPB), and dioctyl sebacate (DOS) were purchased from TCI. 1-Nitro-2-(n-octyloxy) benzene (NPOE) was purchased from Alfa Aesar. An anion excluder, sodium tetraphenylborate (NaTPB), was obtained from Merck, and metal chlorides ($M^{n+}$=$Na^+$, $K^+$, $Mg^{2+}$, $Ca^{2+}$, $Cu^{2+}$, $Fe^{2+}$, $Co^{2+}$, $Zn^{2+}$, and $Pb^{2+}$) from TCI were used without any further purification. Deionized water (18 MΩ) was used to make aqueous solutions.

Instrumentation

Amperometric measurements were performed by using a CHI potentiostat (model #760 E, CHI, Austin, TX, USA). A three-electrode system is comprising a working electrode, an Ag/AgCl reference electrode, and a Pt wire as the counter electrode were used. Potentiometric experiments were performed with a high-impedance unit (Lawson Labs, EMF 6) along with Ag/AgCl (1 M KCl) reference electrodes.

Ionophore Development Strategy

An ionophore should reversibly bind to the analyte with high selectivity and should be insoluble in aqueous solutions to use the ISE in water samples. Because hydrazide derivatives are known to bind $Cu^{2+}$ ions, a benzo hydrazide-modified dendritic structure was developed, along with a cinnamaldehyde modification, to provide a multifunctional molecular probe for $Cu^{2+}$ ions that is effective for both potentiometry and fluorimetry. The dendric molecular component in the molecule makes it hydrophobic, and the attached cinnamaldehyde moiety allows it to be a fluorescent molecular probe.

Synthesis of CMD 3,4,5-Tris(benzyloxy)benzohydrazide (2 g, 0.0044 mol) and N,N-dimethyl cinnamaldehyde (1.0305 g, 0.0057 mol) were dissolved in a $CHCl_3$ (15 mL) and MeOH (45 mL) mixture. The reagent mixtures were stirred at 65° C. for 36 h under $N_2$ atmosphere. After 36 h, the reaction mixture was concentrated in vacuo and the compound purified by flash chromatography over silica gel as the stationary phase. The elution was performed with 15% MeOH in $CHCl_3$ to give the pure product as a yellow solid (experimental yield 55%). $^1H$ NMR (700 MHz, DMSO-$d_6$) δ: 2.97 (s, $CH_3$, 6H), 5.03 (s, $CH_2$, 2H), 5.21 (s, $CH_2$, 4H), 6.85 (dd, J=8.2 Hz, CH, 1H), 6.92 (d, J=15.8 Hz, CH, 1H), 6.72-7.50 (m, ArH & PhH, 21H), 8.20 (d, J=9.2 Hz, CH=N, 1H), 11.47 (s, CONH, 1H) (FIG. 7); $^{13}C$ NMR (175 MHz, DMSO-$d_6$) δ: 70.91, 74.73, 107.26, 112.46, 120.95, 124.09, 128.16, 128.37, 128.44, 128.56, 128.67, 128.94, 129.28, 137.28, 137.88, 140.33, 151.13, 151.18, 152.52, 162.45 (FIG. 8); m. p. 179° C.

UV-Vis Spectroscopy

UV-Vis spectra of the ionophore ($2\times10^{-5}$ M) were obtained in a methanol solution. The UV-Vis absorption spectrum showed a characteristic peak of cinnamaldehyde centered at 387 nm. Job's plot was obtained to quantify the metal-to-ligand binding stoichiometry. Furthermore, the binding constant was acquired in a separate experiment by varying the stoichiometry between the metal and the ligand, and the Benesi-Hildebrand plot was obtained to calculate the binding constant from the slope of the plot.

Fluorescence Characterization and Quantifications of Cu (II)

The ionophore ($2\times10^{-5}$ M) showed strong fluorescence emission centered at 520 nm when excited at 387 nm. The fluorescence response was tested in the presence of different metal ions in a 1:1 mol equivalent ratio to find the selectivity of the molecular probe toward $Cu^{2+}$. A calibration plot was obtained with varying concentrations of $Cu^{2+}$ ions by using fluorescence intensity, which demonstrates the ability of the ionophore to act as a molecular fluorescence probe.

FT-IR Characterization

The FT-IR spectrum of the 10 mM of CMD and CMD with $Cu^{2+}$ ions (1:1 mol ratio) was obtained using an FTIR spectrometer (PerkinElmer, Model: Spectrum II). The analyte solution was drop casted on a potassium bromide crystal optic disc (purchased from Alfa Aesar).

Fabrication of $Cu^{2+}$ Microsensor

A borosilicate glass capillary (o.d. 1.5 mm, i.d. 0.86 mm) was first pulled with a pipette puller (Sutter Instruments, Novato, CA, USA), and then polished to obtain an inner tip diameter of 25 μm (RG<2) to make a $Cu^{2+}$ ion-selective microprobe. After optimization of the membrane components, the best ratio of the membrane components was determined. The ion-selective cocktail was prepared by mixing 10% ionophore, 2.8% tetraphenylborate, 3% PVC, 30% DOS, 54.2% Vulcan carbon powder, and 500 μL tetrahydrofuran (THF). The composition was mixed thoroughly with a glass rod on a watch glass until all THF evaporated. An extra 40.00% of DOS was further added to the membrane components to maintain consistency in a sensor paste. The pulled capillary was then backfilled with the sensor paste and pushed it to the pulled end with a Cu wire. To make electrical contact between the sensor paste and the inserted Cu wire, 5.00% Vulcan carbon in a DOS mixture was added to the pipette from the back-opening side. The Cu wire connection was secured by applying 10 min epoxy to the junction of the capillary end and the Cu wire. The sensor tip was polished with lens cleaning paper and cured overnight in 1 mM $CuCl_2$ solution before the calibration of the Cu (II) microsensor.

Measurement Selectivity Coefficients

The selectivity coefficients against different metal ions were determined by the mixed solution (fixed interference) method. Background concentrations of $10^{-2}$ M solution for alkaline earth and transition metal cations and $10^{-1}$ M for alkali metal cations were used.

Drinking Water Sample Preparation

The water samples (tap water at Oregon State University, Corvallis, USA) were pretreated by filtering with Whatman #1 filter paper, and then the pH was adjusted to 5.5 by using 1 M HCl. The measurement was carried out three times by using both potentiometry and atomic absorption spectroscopy after the calibration.

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound having formula (I):

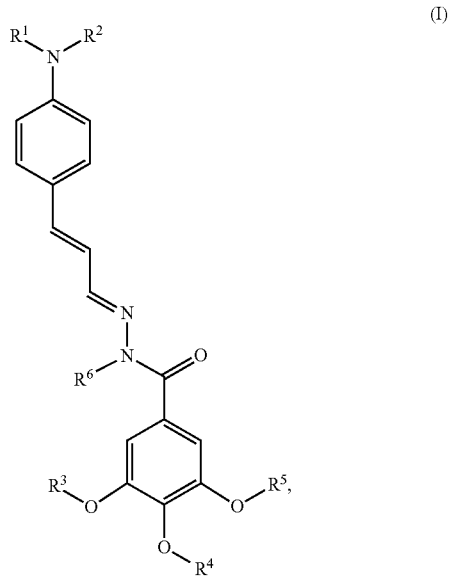

or a salt, an isomer, or tautomer thereof, wherein:
$R^1$, $R^2$, and $R^6$ are independently H, optionally substituted C1-C18 alkyl, C1-C18 optionally substituted C6-C18 aryl, or optionally substituted C5-C18 heteroaryl, and $R_3$, $R_4$, and $R_5$ are C1-C18 alkyl substituted with a C6-C18 aryl or a C5-C18 heteroaryl.

2. The compound of claim 1, wherein $R^3$, $R^4$, and $R^5$ are independently optionally substituted benzyl.

3. The compound of claim 1, wherein $R_3$, $R_4$, and $R_5$ are benzyl.

4. The compound of claim 1, wherein $R^1$ and $R^2$ are independently H, methyl, or ethyl.

5. The compound of claim 1, wherein $R^1$ and $R^2$ are methyl and $R^6$ is H.

6. The compound of claim 1, wherein the compound is:

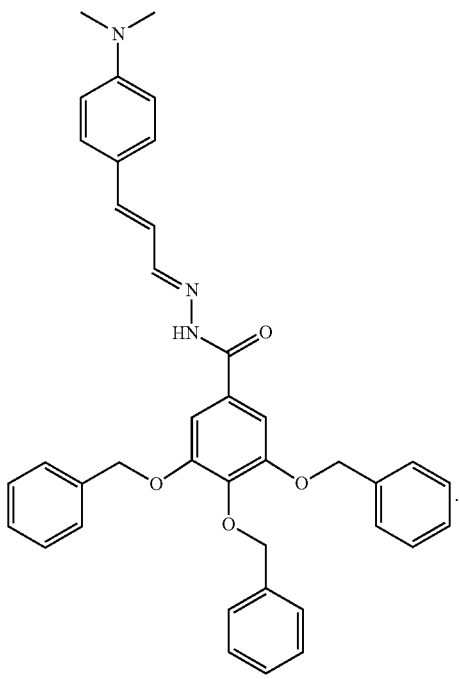 [SMILES: CN(C)c1ccc(/C=C/C=N/NC(=O)c2cc(OCc3ccccc3)c(OCc3ccccc3)c(OCc3ccccc3)c2)cc1]

7. A carbon-based membrane comprising a compound of claim 1 bound to the membrane.

8. The membrane of claim 7, wherein the compound is bound covalently or non-covalently.

9. A sensor comprising the membrane of claim 7.

10. The sensor of claim 9, wherein the sensor is a potentiometric, fluorimetric, or colorimetric sensor.

11. The sensor of claim 9, wherein the sensor is a potentiometric sensor with Cu2+ ion detection limit of about 3.5 μM and/or a fluorimetric sensor with Cu2+ ion detection limit of about 15 nM.

12. A Cu2+-selective electrode comprising a solid electron conductor in electrical contact with an ion-selective polymeric composition comprising a compound of claim 1.

13. The electrode of claim 12, wherein the solid electron conductor is a copper wire.

14. The electrode of claim 12, wherein the ion-selective polymeric composition further comprises: (a) tetraphenyl borate, tetrakis(4-chlorophenyl) borate, tetrakis [3,4-bis(trifluoromethyl) phenyl] borate, or a combination thereof; (b) polyvinyl chloride (PVC); (c) dioctyl sebacate (DOS), 1-nitro-2-(n-octyloxy) benzene (NPOE), or a combination thereof; and (d) carbon.

15. The electrode of claim 12, wherein the ion-selective polymeric composition further comprises tetraphenylborate, PVC, DOS, and Vulcan carbon powder.

16. A colorimetric device comprising a membrane impregnated with a compound of claim 1.

17. The colorimetric device of claim 16, wherein the membrane is a cellulose membrane.

18. A carbon-based membrane comprising a compound bound to the membrane, wherein the compound has formula (I):

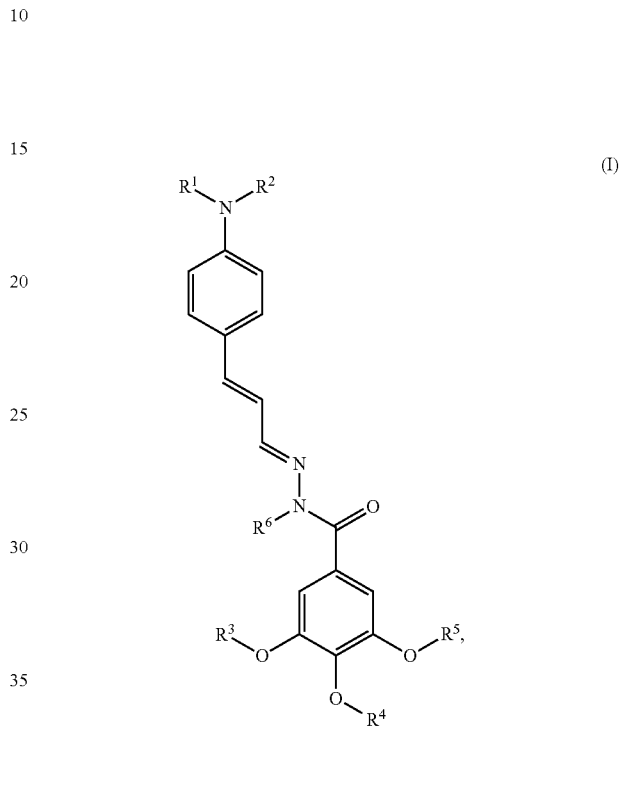

or a salt, an isomer, or tautomer thereof, wherein:

$R^1$, $R^2$, and $R^6$ are independently H, optionally substituted C1-C18 alkyl, C1-C18 optionally substituted C6-C18 aryl, or optionally substituted C5-C18 heteroaryl, and $R^3$, $R^4$, and $R^5$ are C1-C18 alkyl optionally substituted with a C6-C18 aryl or a C5-C18 heteroaryl.

19. The membrane of claim 18, wherein the compound is bound covalently or non-covalently.

20. A sensor comprising the membrane of claim 18.

21. The sensor of claim 20, wherein the sensor is a potentiometric, fluorimetric, or colorimetric sensor.

22. The sensor of claim 20, wherein the sensor is a potentiometric sensor with Cu2+ ion detection limit of about 3.5 μM and/or a fluorimetric sensor with Cu2+ ion detection limit of about 15 nM.

23. A Cu2+-selective electrode comprising a solid electron conductor in electrical contact with an ion-selective polymeric composition comprising a compound, wherein the compound has formula (I):

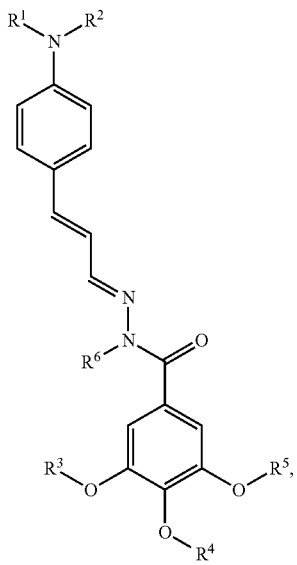

or a salt, an isomer, or tautomer thereof, wherein:

$R^1$, $R^2$, and $R^6$ are independently H, optionally substituted C1-C18 alkyl, C1-C18 optionally substituted C6-C18 aryl, or optionally substituted C5-C18 heteroaryl, and $R^3$, $R^4$, and $R^5$ are C1-C18 alkyl optionally substituted with a C6-C18 aryl or a C5-C18 heteroaryl.

24. The electrode of claim 23, wherein the solid electron conductor is a copper wire.

25. The electrode of claim 23, wherein the ion-selective polymeric composition further comprises: (a) tetraphenyl borate, tetrakis(4-chlorophenyl) borate, tetrakis [3,4-bis(trifluoromethyl) phenyl] borate, or a combination thereof; (b) polyvinyl chloride (PVC); (c) dioctyl sebacate (DOS), 1-nitro-2-(n-octyloxy) benzene (NPOE), or a combination thereof; and (d) carbon.

26. The electrode of claim 23, wherein the ion-selective polymeric composition further comprises tetraphenylborate, PVC, DOS, and Vulcan carbon powder.

27. A colorimetric device comprising a membrane impregnated with a compound, wherein the compound has formula (I):

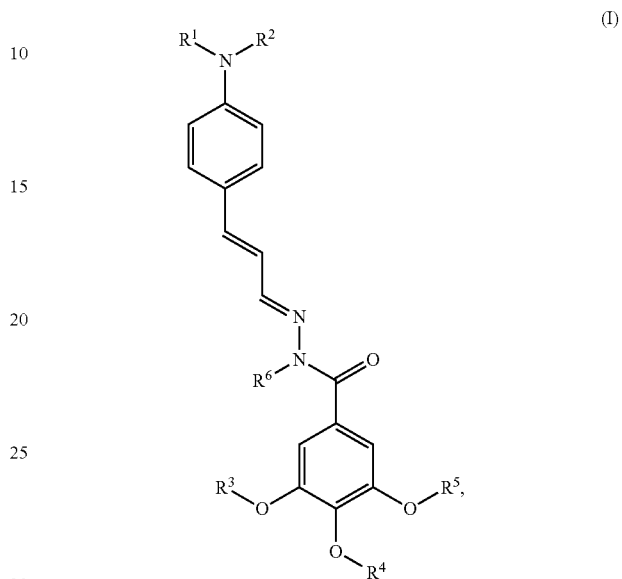

or a salt, an isomer, or tautomer thereof, wherein:

$R^1$, $R^2$, and $R^6$ are independently H, optionally substituted C1-C18 alkyl, C1-C18 optionally substituted C6-C18 aryl, or optionally substituted C5-C18 heteroaryl, and $R^3$, $R^4$, and $R^5$ are C1-C18 alkyl optionally substituted with a C6-C18 aryl or a C5-C18 heteroaryl.

28. The colorimetric device of claim 27, wherein the membrane is a cellulose membrane.

* * * * *